(12) United States Patent
Cohen-Kaminsky et al.

(10) Patent No.: US 11,376,245 B2
(45) Date of Patent: Jul. 5, 2022

(54) DIZOCILPINE DERIVATIVES AS PERIPHERAL NMDA RECEPTOR ANTAGONISTS

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); UNIVERSITE PARIS SUD, Orsay (FR); ASSISTANCE PUBLIQUE-HOPITAUX DE PARIS (APHP), Paris (FR); HOPITAL MARIE LANNELONGUE, Le Plessis-Robinson (FR)

(72) Inventors: Sylvia Cohen-Kaminsky, Le Plessis-Robinson (FR); Marc Humbert, Le Plessis-Robinson (FR); Sebastien Dumas, Le Plessis-Robinson (FR); Gilles Bru-Mercier, Le Plessis-Robinson (FR); Samir Messaoudi, Chatenay-Malabry (FR); Jean-Daniel Brion, Chatenay-Malabry (FR); Mouad Alami, Chatenay-Malabry (FR); Gilles Galvani, Chatenay-Malabry (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); UNIVERSITE PARIS SUD, Orsay (FR); ASSISTANCE PUBLIQUE—HOPITAUX DE PARIS (APHP), Paris (FR); HOPITAL MARIE LANNELONGUE, Le Plessis-Robinson (FR)

( * ) Notice: Subject to any disclaimer, the term of this patent is extended or adjusted under 35 U.S.C. 154(b) by 0 days.

(21) Appl. No.: 16/308,654

(22) PCT Filed: Jun. 13, 2017

(86) PCT No.: PCT/EP2017/064409
§ 371 (c)(1),
(2) Date: Dec. 10, 2018

(87) PCT Pub. No.: WO2017/216159
PCT Pub. Date: Dec. 21, 2017

(65) Prior Publication Data
US 2019/0307738 A1    Oct. 10, 2019

(30) Foreign Application Priority Data
Jun. 13, 2016 (EP) .................... 16305712

(51) Int. Cl.
C07D 451/02 (2006.01)
A61K 31/46 (2006.01)
A61P 9/12 (2006.01)
A61K 45/06 (2006.01)
C07D 451/00 (2006.01)

(52) U.S. Cl.
CPC ............. *A61K 31/46* (2013.01); *A61K 45/06* (2013.01); *A61P 9/12* (2018.01); *C07D 451/00* (2013.01); *C07D 451/02* (2013.01)

(58) Field of Classification Search
CPC .......... C07D 451/02; A61K 31/46; A61P 9/12
USPC ........................................... 546/74; 514/289
See application file for complete search history.

(56) References Cited

PUBLICATIONS

Ahmed et al., "N-Methyl-D-Aspartate, etc.," Expert Opinion on Therapeutic Patents, 30(10), 743-767. (Year: 2020).*
Capuco et al., "A Comprehensive, etc.," Current Pain and Headache Reports 24:41, 1-12. (Year: 2020).*
Hayashi et al., "Effects of neural, etc.," Journal of Biomedical Science, 27:29, 1-11. (Year: 2020).*
Kreutzwiser et al., "Expanding Role of NMDA, etc.," CNS Drugs, 33, 347-374. (Year: 2019).*
Simone, Oncology: Introduction, Cecil Textbook of Medicine, ed Bennett et al. W.B. Saunders CO 20th ed, vol. 1, pp. 1004-1010 (Year: 1996).*
Gura, Systems for Identifying New Drugs Are Often Faulty, Cancer Models, Science, 278(5340), pp. 1041-1042. (Year: 1997).*
Johnson et al., Relationships between drug activity in NCI in vitro and in vivo and early clinical trials, British Journal of Cancer 64(10): 1424-1431. (Year: 2001).*

(Continued)

*Primary Examiner* — Charanjit Aulakh
(74) *Attorney, Agent, or Firm* — Oblon, McClelland, Maier & Neustadt, L.L.P.

(57) ABSTRACT

The present invention relates to compounds of formula (I) for use as peripheral NMDA receptor antagonists.

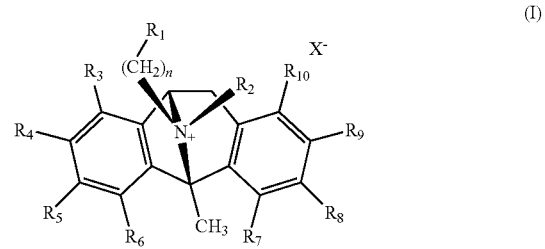

14 Claims, 2 Drawing Sheets

(56) References Cited

PUBLICATIONS

Figure 1:
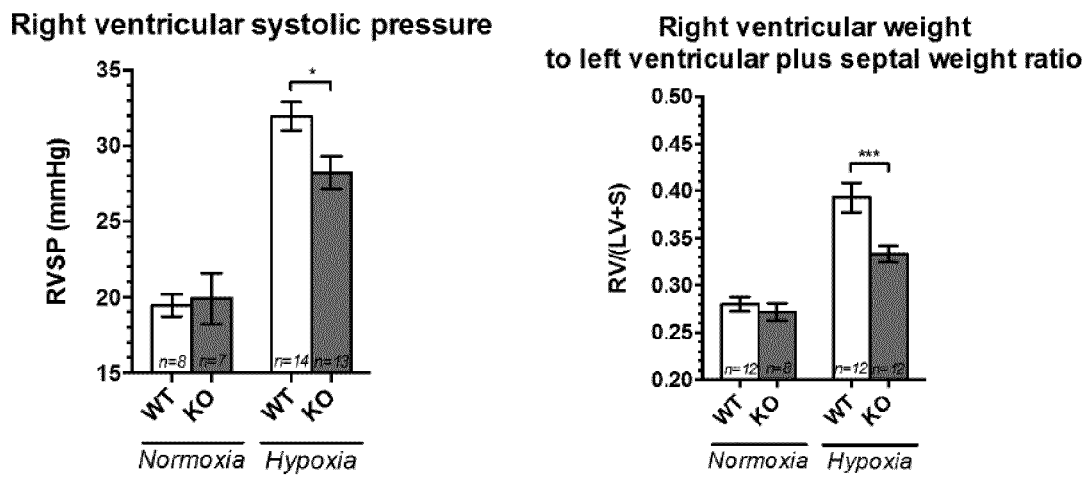

Hanada, "Ionotrophic Glutamate, etc.," Biomolecules, 20, 464, 1-22. (Year: 2020).*
Pearce et al., "Failure modes, etc.," Cancer Drug Design and Discovery, ed. Stephen Neidle, Chapter 18, pp. 424-435. (Year: 2008).*
Jordan, V.C., "Tamoxifen: A Most, etc.," Nature review: Drug Discovery, 2, 205-213. (Year: 2003).*
International Search Report dated Jul. 12, 2017 in PCT/EP2017/064409, 3 pages.
European Search Report dated Dec. 2, 2016 in Patent Application No. 16305712, 2 pages.
Linders, J.T.M. et al. "Synthesis and Preliminary Biochemical Evaluation of Novel Derivatives of PCP" Letters in Drug Design and Discovery, vol. 7, No. 2, XP009192463, 2010, pp. 79-87.
Thompson, W.J. et al. "Synthesis and Pharmacological Evaluation of a Series of Dibenzo[a,d]cycloalkenimines as N-Methyl-D-aspartate Antagonists" Journal of Medicinal Chemistry, American Chemical Society, vol. 33, No. 2, XP002764375, 1990, pp. 789-808.
Memezawa, H. et al. "Hyperthermia nullifies the ameliorating effect of dizocilpine maleate (MK-801) in focal cerebral ischemia" Brain Research, Elsevier, vol. 670, No. 1, XP022256910, 1995, pp. 48-52.
Nagpal et al., "Drug targeting to brain: a systematic approach to study the factors, parameters and approaches for prediction of permeability of drugs across BBB", Expert Opin. Drug Deliv., vol. 10, 30 pages, Jan. 2013.
Doran et al., "The Impact of P-Glycoprotein on the Disposition of Drugs Targeted for Indications of the Central Nervous System: Evaluation Using the MDR1A/1B Knockout Mouse Model", Drug Metabolism and Disposition, vol. 33, pp. 165-174, Dec. 2005.
Office Action dated Aug. 12, 2021 in Chinese Patent Application No. 201780049508.2, filed Jun. 13, 2017, 13 pages (with English Translation).

* cited by examiner

DIZOCILPINE DERIVATIVES AS PERIPHERAL NMDA RECEPTOR ANTAGONISTS

The present invention relates to the identification of novel dizocilpine derivatives and to the use of such compounds as peripheral NMDA (N-Methyl-D-Aspartate) receptor antagonists in particular for the treatment of pulmonary hypertension (PH), and preferably for the treatment of pulmonary arterial hypertension (PAH).

Pulmonary hypertension defines a group of clinical conditions presenting wry circulation pressure. Thus, a normal mean pulmonary artery pressure (mPAP) at rest is 14±3.3 mm Hg, and a PH is commonly defined as an increase of mPAP≥25 mm Hg at rest, as assessed by right heart catheterization. The PH diseases are classified into five classes: class 1 to class 5 (*Management of pulmonary arterial hypertension.* McLaughlin V. V., Shah S. J., Souza R., Humbert M., *J. Am. Coll. Cardiol.*, 2015 May 12; 65(18): 1976-97). In particular, pulmonary hypertension diseases include pulmonary arterial hypertension (group 1), such as pulmonary veno-occlusive disease and/or pulmonary capillary hemangomatosis, PH due to left heart disease (group 2), PH due to lung diseases and/or hypoxia (group 3), chronic thromboembolic pulmonary hypertension (group 4), and other PH conditions with unclear multifactorial mechanisms (group 5).

Among pulmonary hypertension diseases, the pulmonary arterial hypertension is a devastating pulmonary vascular disease causing breathlessness, loss of exercise capacity and ultimately death. As recently, pointed by the inventors, this disease is characterized by a chronic increase in pulmonary artery pressure (above 25 mmHg), caused by an important remodeling of small pulmonary vessels associated to inflammation, leading to progressive vessel occlusion, ultimately leading to right ventricular failure and death (Cohen-Kaminsky S et al., *Drug Discovery Today* 2014, Huertas A, et al., *Circulation,* 2014).

There is unfortunately no cure of PAH. The current PAH therapies are essentially focused on decreasing pulmonary vascular resistance by stimulating pulmonary vasodilation (prostacyclin analogues, phosphodiesterase type 5 inhibitors, and endothelin receptor antagonists) (Humbert et al., *N. Engl. J. Med.* 2004, O'Callaghan D S, et al. *Nat. Rev. Cardiol.,* 2014). These agents have some anti-remodeling properties, but there is no current anti-remodelling strategy approved for PAH. In spite of these treatments targeting endothelial cell dysfunction that are now available to improve quality of life and survival, in most patients the outcome is very poor. Median survival of PAH (that was 2.8 years in the 1980's) remains inferior to 5 years and refractory cases are candidates for heart-lung transplantation, a major surgery with current limitations due to shortage of organ donors and severe long-term complications (5-year survival is only 50%). Some hemodynamic and clinical effects of the tyrosine kinase inhibitor imatinib have also been reported in severe PAH, but at the expense of severe side effects.

Therefore, the discovery of new treatments targeting other PAH pathomechanisms would be useful to slow, stop, or even reverse disease progression.

In PAH, right heart failure is secondary to extensive remodeling and progressive obstruction of small pulmonary vessels, a complex and multifactorial process involving uncontrolled smooth muscle cell proliferation. Endothelial cell dysfunction is thought to mediate structural changes in the pulmonary vasculature, yet it is increasingly evident that inflammation plays a role in PAH pathogenesis (Price et al., *Chest,* 2012). It has been established that i) inflammation influences vascular remodeling and (ii) immune dysfunction and autoimmunity may contribute to the pathophysiology of PAH (Perros et al., *Am. J. Respir. Crit. Care Med.* 2012, *Med. Sci.* 2013, *Am. J. Respir. Crit. Care Med.,* 2013).

Recently, the inventors of the present invention demonstrated that NMDA receptors contributes to pulmonary remodeling and thus, have a role in the development of pulmonary hypertension.

It is reminded that the NMDA receptor has been first discovered in the central nervous system playing a role in neurotransmission, neuronal plasticity and learning and memory. In addition it is involved in neurodegenerative diseases, such as Alzheimer disease and stroke.

More precisely, NMDA receptor is a specific type of ionotropic glutamate receptor with a high permeability to calcium and a unique feature of controlling numerous calcium-dependent processes, such as cell proliferation. Functional NMDA receptors are tetrameric assemblies composed of multiple GluN1 subunits in combination with at least one type of GluN2 to generate a large number of different NMDARs.

One way in which the functions of the various NMDAR subunits may be assessed is through the use of subunit selective agonists and antagonists and a number of pharmacological agents have already been shown to distinguish between certain NMDAR subtypes. Memantine, MK-801 (dizocilpine), dextrophan, aptiganel, ifenprodil, Ro-25-6981 are for example representative NMDAR antagonists.

It is now known that NMDARs also play a role outside the CNS in various peripheral systems, including bone, pancreas and skin, where they play important functions such as regulation of the bone mass, liberation of insulin and skin development (Skerry T M, Genever P G. *Trends Pharmacol. Sci.,* 2001), and kidney function (Dryer S, *Nephrol. Dial. Transplant.,* 2015). The expression of NMDA receptors has also been characterized in the peripheral tissues, including the lung, the heart and the immune system.

At last, several studies have shown the utility of NMDA receptor antagonists to limit tumor growth (Takano T et al., *Nature Medicine,* 2001, Rothstein J D et al., *Nature Medicine,* 2001, Rzeski W et al., *PNAS,* 2001). However, NMDA receptor expression is not limited to glioblastoma and many tumors may express NMDA receptors.

Thus, NMDARs have a preeminent role in many physiological and pathological processes outside the CNS.

However, at the knowledge of the inventors there is no information available about the development of peripheral NMDAR antagonists.

Otherwise, since the NMDA receptor has been first discovered in the CNS, the available NMDA receptor blockers, like in particular memantine and ifenprodil, are essentially provided as neuroprotective drugs that are useful in stroke, traumatic brain injury, epilepsy, Alzheimer disease, Parkinson disease, Huntington's chorea, and others involving the brain and or the spinal cord tissue.

Accordingly, NMDA receptor blockers produced so far are mainly designed and used with the intention that they will cross the blood brain barrier in order to treat neurological diseases.

Unfortunately, general blocking of NMDA receptors that could reach the brain causes adverse effects such as ataxia, memory deficit, hallucination, cognitive disruption, psychotic-spectrum reaction and other neurological problems.

In particular, it is well known that the administration of antagonist Dizocilpine causes psychotomimetic side effects, such as hallucinations, or hyperlocomotions (Joannes T. M. Lindens et al., *Letters in Drug Design & Discovery*, 2010, 7, 79-87). It also induces brain lesions called Olney's lesions, in test rats.

For these reasons, the antagonist Dizocilpine is mainly used in an animal model to mimic psychosis for experimental purposes.

Thus, to date, most NMDAR antagonists that reached clinical development to treat neurodegenerative diseases cannot be used in the periphery without major central side-effects.

Indeed, it is not acceptable to use such drugs for treating a chronic disease with peripheral NMDAR involvement, such as pulmonary hypertension and in particular pulmonary arterial hypertension with secondary deleterious toxic side effects on healthy brain tissues.

Therefore, there is a crucial need for new peripheral NMDAR blockers.

In particular, there is a need for new compounds selectively targeting the peripheral NMDA receptor but not crossing the blood brain barrier. However, a minimized brain penetration to reduce undesirable CNS side-effects has not to be obtained in detriment of the expected peripheral NMDARs blocking activity.

Furthermore, there is a need for new compounds acting as selective antagonists toward NMDARs, not crossing the blood-brain barrier and having a good aqueous solubility to be convenient at least for administration.

More particularly, there is a need to provide new means of treating a disease with peripheral NMDAR involvement, such as pulmonary hypertension and in particular pulmonary arterial hypertension.

The present invention precisely aims to provide novel compounds complying with the previous requirements.

Therefore, according to one of its aspects, the invention is directed to compounds of formula (I):

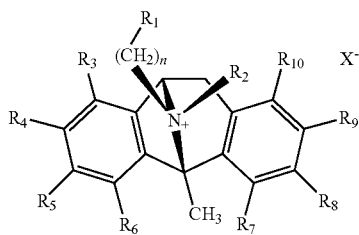

wherein:

$R_1$ represents a hydrogen atom, a halogen atom, —OH, —CN, a $(C_1-C_6)$alkyl group, a $(C_2-C_6)$alkenyl group, a $(C_1-C_4)$alkoxy group, a —C(=NH)(—OH) group, a $(C_1-C_4)$alkyl-C(=NH)(—OH) group, a —NH—CO—$(C_1-C_4)$ alkyl group, a —$NR_{11}R_{12}$ group, a —$N^+R_{13}R_{14}R_{15}$ group, a $(C_3-C_7)$cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, $(C_1-C_6)$alkyl group, $(C_1-C_4)$alkoxy group, or trifluoromethyl group;

$R_2$ represents a $(C_1-C_{10})$alkyl group, a $(C_1-C_6)$alkyl-OH group, a $(C_2-C_6)$alkenyl group or a $(C_2-C_6)$alkynyl group;

n is 1, 2, 3, 4 or 5;

$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a $(C_1-C_6)$ alkyl group, a $(C_1-C_6)$alkoxy group, a $(C_1-C_6)$alkyl-OH group, a —$NR_{11}R_{12}$ group, a —$N^+R_{13}R_{14}R_{15}$ group, a 5- or 6-membered aryl group or a 5- to 12-membered heteroaryl group;

$R_{11}$, $R_{12}$, $R_{13}$, $R_{14}$, and $R_{15}$ represent, independently of each other, a hydrogen atom or a $(C_1-C_6)$alkyl group;

$X^-$ is an anionic counterion, in particular chosen from $I^-$, $Cl^-$, $Br^-$, and $OH^-$;

for use as a peripheral NMDA receptor antagonist.

Preferably, according to one of its aspects, the invention is directed to compounds of formula (I):

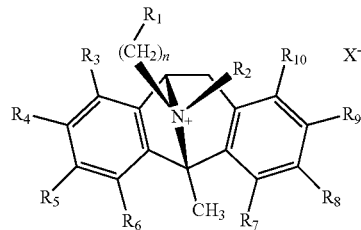

wherein:

$R_1$ represents a hydrogen atom, —OH, —CN, a $(C_1-C_6)$ alkyl group, a $(C_1-C_4)$alkoxy group, a —C(=NH)(—OH) group, a $(C_1-C_4)$alkyl-C(=NH)(—OH) group, a —NH—CO—$(C_1-C_4)$alkyl group, a —$NR_{11}R_{12}$ group, a —$N^+R_{13}R_{14}R_{15}$ group, a $(C_3-C_7)$cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, $(C_1-C_6)$alkyl group, $(C_1-C_4)$alkoxy group, or trifluoromethyl group;

$R_2$ represents a $(C_1-C_{10})$alkyl group;

n is 1, 2, 3, 4 or 5;

$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a $(C_1-C_6)$ alkyl group, a $(C_1-C_6)$alkoxy group, a $(C_1-C_6)$alkyl-OH group, a —$NR_{11}R_{12}$ group, a —$N^+R_{13}R_{14}R_{15}$ group, a 5- or 6-membered aryl group or a 5- to 12-membered heteroaryl group;

$R_{11}$, $R_{12}$, $R_{13}$, $R_{14}$, and $R_{15}$ represent, independently of each other, a hydrogen atom or a $(C_1-C_6)$alkyl group;

$X^-$ is an anionic counterion, in particular chosen from $I^-$, $Cl^-$, $Br^-$, and $OH^-$;

for use as a peripheral NMDA receptor antagonist.

As detailed here-after, the inventors identified some chemical modifications which, when introduced in the parent molecule dizocilpine, allow to achieve compounds, new for some of them, that are advantageously unable to cross the blood brain barrier but still exhibit a selective and efficient peripheral NMDARs blocking activity.

As shown in the following examples, compounds according to formula (I) may advantageously have a Kp brain value measured in rat very low, by contrast to dizocilpine which has a much greater Kp brain value.

It is reminded that in vivo equilibrium distribution between blood and brain in rodents is the most commonly used parameter to evaluate brain penetration. This parameter is defined as the ratio of concentrations in brain and blood, $Kp_{"brain"}$ ($C_{brain}/C_{plasma}$) or log (BB).

Log(BB) is the logarithm of the ratio of the steady-state total concentration of a compound in the brain to that in the blood/plasma, $\log(BB) = \log(C_{brain}/C_{plasma})$.

This parameter depends upon the passive diffusion characteristics, the implication of membrane transporters at the BBB level and the relative drug binding affinity differences between the plasma proteins and brain tissue.

Generally, compounds with a brain/plasma ratio of greater than 0.5 are considered to have sufficient access to the central nervous system (CNS). Thus, compounds with a value greater than 1 freely cross the BBB. As shown in the following example 3, claimed compounds do not penetrate the central nervous system (CNS) in rat.

Thus, this property of not crossing the BBB is advantageously not deleterious for the expected selective peripheral NMDARs blocking activity.

Accordingly, the compounds according to the invention may be used as selective peripheral NMDA receptor antagonist for treating, without central side-effects, the conditions and diseases with peripheral NMDA receptors involvement. Advantageously, they target peripheral NMDARs in the three systems (cardiac, pulmonary, immune), notably involved in PH, and in particular in PAH, without central side-effects.

According to the invention, the term "central side-effects" encompasses adverse effects in particular on healthy brain tissus, such as ataxia, memory deficit, hallucination, cognitive disruption, psychotic-spectrum reaction and other neurological problems.

According to another of its aspects, the present invention also relates to compounds of general formula (I):

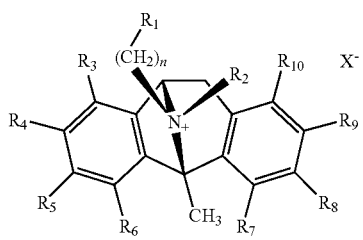

wherein:
$R_1$ represents a hydrogen atom, a halogen atom, —OH, —CN, a ($C_1$-$C_6$)alkyl group, a ($C_2$-$C_6$)alkenyl group, a ($C_1$-$C_4$)alkoxy group, a —C(=NH)(—OH) group, a ($C_1$-$C_4$)alkyl-C(=NH)(—OH) group, a —NH—CO—($C_1$-$C_4$) alkyl group, a —$NR_{11}R_{12}$ group, a —$N^+R_{13}R_{14}R_{15}$ group, a ($C_3$-$C_7$)cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, ($C_1$-$C_6$)alkyl group, ($C_1$-$C_4$)alkoxy group, or trifluoromethyl group;
$R_2$ represents a ($C_1$-$C_{10}$)alkyl group, a ($C_1$-$C_6$)alkyl-OH group, a ($C_2$-$C_6$)alkenyl group or a ($C_2$-$C_6$)alkynyl group;
n is 1, 2, 3, 4 or 5;
$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a ($C_1$-$C_6$) alkyl group, a ($C_1$-$C_6$)alkoxy group, a ($C_1$-$C_6$)alkyl-OH group, a —$NR_{11}R_{12}$ group, a —$N^+R_{13}R_{14}R_{15}$ group, a 5- or 6-membered aryl group or a 5- to 12-membered heteroaryl group;
$R_{11}$, $R_{12}$, $R_{13}$, $R_{14}$, and $R_{15}$ represent, independently of each other, a hydrogen atom or a ($C_1$-$C_6$)alkyl group;
$X^-$ is an anionic counterion, in particular chosen from $I^-$, $Cl^-$, $Br^-$, and $OH^-$;
provided that when $R_2$ is a methyl group, $R_3$, $R_4$, $R_5$, $R_6$, $R_7$, $R_8$, $R_9$ and $R_{10}$ are a hydrogen atom and n is 1, then $R_1$ is not a hydrogen atom.

Preferably, the present invention also relates to compounds of general formula

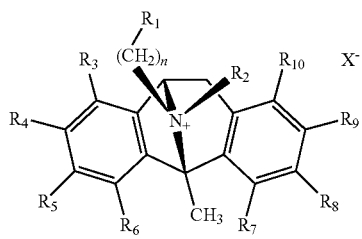

wherein:
$R_1$ represents a hydrogen atom, —OH, —CN, a ($C_1$-$C_6$) alkyl group, a ($C_1$-$C_4$)alkoxy group, a —C(=NH)(—OH) group, a ($C_1$-$C_4$)alkyl-C(=NH)(—OH) group, a —NH—CO—($C_1$-$C_4$)alkyl group, a —$NR^{11}R^{12}$ group, a —$N^+R_{13}R_{14}R_{15}$ group, a ($C_3$-$C_7$)cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, ($C_1$-$C_6$)alkyl group, ($C_1$-$C_4$)alkoxy group, or trifluoromethyl group;
$R_2$ represents a ($C_1$-$C_{10}$)alkyl group;
n is 1, 2, 3, 4 or 5;
$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a ($C_1$-$C_6$) alkyl group, a ($C_1$-$C_6$)alkoxy group, a ($C_1$-$C_6$)alkyl-OH group, a —$NR_{11}R_{12}$ group, a —$N^+R_{13}R_{14}R_{15}$ group, a 5- or 6-membered aryl group or a 5- to 12-membered heteroaryl group;
$R_{11}$, $R_{12}$, $R_{13}$, $R_{14}$, and $R_{15}$ represent, independently of each other, a hydrogen atom or a ($C_1$-$C_6$)alkyl group;
$X^-$ is an anionic counterion, in particular chosen from $I^-$, $Cl^-$, $Br^-$, and $OH^-$;
provided that when $R_2$ is a methyl group, $R_3$, $R_4$, $R_5$, $R_6$, $R_7$, $R_8$, $R_9$ and $R_{10}$ are a hydrogen atom and n is 1, then $R_1$ is not a hydrogen atom.

According to another of its aspects, the invention is directed to compounds of formula (I) according to the invention for use for preventing and/or inhibiting and/or treating a disease or a condition in which the peripheral NMDA receptors are involved, like pulmonary hypertension diseases and in particular pulmonary arterial hypertension.

According to the present invention, pulmonary hypertension diseases cover any pathologies trouble commonly identified under that name. According to this aspect, the present invention also covers any new group or subgroup of pulmonary arterial hypertension and pulmonary hypertension, in particular as mentioned hereafter.

According to another of its aspects, the present invention is directed to a method of treatment and/or prevention of a disease or a condition in which the peripheral NMDA receptors are involved, like pulmonary hypertension diseases and in particular pulmonary arterial hypertension, comprising the administration of a compound of formula (I) according to the invention.

Advantageously, the present invention is directed to a method of prevention of a disease or a condition in which the peripheral NMDA receptors are involved, like pulmonary hypertension diseases and in particular pulmonary arterial hypertension, comprising the administration of a compound of formula (I) according to the invention.

Indeed, compounds of formula (I) of the present invention are very useful as vascular protectors in prevention, for example in pre-operative or in the prevention of inflammation phenomena in extracorporeal circulation (ECC).

Within the meaning of the invention, the term "prevent" or "prevention" with respect to an event is intended to mean the decrease of a risk of occurrence of said event.

In the context of the present invention, the following abbreviations and empirical formulae are used:
ALI Acute Lung Injury
ARDS Acute Respiratory Distress Syndrome
BB Brain and Blood
BBB Blood-Brain Barrier
$CDCl_3$ Deuterated chloroform
CNS Central Nervous System
DMSO Dimethyl Sulfoxide
IR InfraRed
hPASMC Human Pulmonary Arterial Smooth Muscle Cells
HRMS High Resolution Mass Spectroscopy
$LiAlH_4$ or LAH Lithium Aluminium Hydride
$Na_2SO_4$ Sodium Sulfate
NMDA N-Methyl-D-Aspartate
NMDAR N-Methyl-D-Aspartate Receptor
NMR Nuclear Magnetic Resonance
PAH Pulmonary Arterial Hypertension
PH Pulmonary Hypertension
RT-PCR Reverse Transcription Polymerase Chain Reaction
RVSP Right Ventricular Systolic Pressure
THF Tetrahydrofuran
TLC Thin Layer Chromatography
VWF Von Willebrand Factor Other features and advantages of the invention will emerge more clearly from the description and examples that follow.

Compounds of the Invention

As above-mentioned, the compounds used according to the invention correspond to general formula (I):

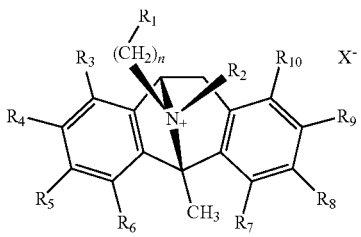

wherein:
$R_1$ represents a hydrogen atom, a halogen atom, —OH, —CN, a ($C_1$-$C_6$)alkyl group, a ($C_2$-$C_6$)alkenyl group, a ($C_1$-$C_4$)alkoxy group, a —C(=NH)(—OH) group, a ($C_1$-$C_4$)alkyl-C(=NH)(—OH) group, a —NH—CO—($C_1$-$C_4$)alkyl group, a —$NR_{11}R_{12}$ group, a —$N^+R_{13}R_{14}R_{15}$ group, a ($C_3$-$C_7$)cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, ($C_1$-$C_6$)alkyl group, ($C_1$-$C_4$)alkoxy group, or trifluoromethyl group;

$R_2$ represents a ($C_1$-$C_{10}$)alkyl group, a ($C_1$-$C_6$)alkyl-OH group, a ($C_2$-$C_6$)alkenyl group or a ($C_2$-$C_6$)alkynyl group;
n is 1, 2, 3, 4 or 5;
$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a ($C_1$-$C_6$) alkyl group, a ($C_1$-$C_6$)alkoxy group, a ($C_1$-$C_6$)alkyl-OH group, a —$NR_{11}R_{12}$ group, a —$N^+R_{13}R_{14}R_{15}$ group, a 5- or 6-membered aryl group or a 5- to 12-membered heteroaryl group;
$R_{11}$, $R_{12}$, $R_{13}$, $R_{14}$, and $R_{15}$ represent, independently of each other, a hydrogen atom or a ($C_1$-$C_6$)alkyl group;
$X^-$ is an anionic counterion, in particular chosen from $I^-$, $Cl^-$, $Br^-$, and $OH^-$.

Preferably, the compounds used according to the invention correspond to general formula (I):

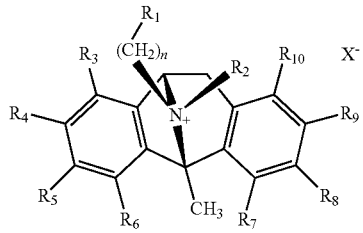

wherein:
$R_1$ represents a hydrogen atom, —OH, —CN, a ($C_1$-$C_6$) alkyl group, a ($C_1$-$C_4$)alkoxy group, a —C(=NH)(—OH) group, a ($C_1$-$C_4$)alkyl-C(=NH)(—OH) group, a —NH—CO—($C_1$-$C_4$)alkyl group, a —$NR_{11}R_{12}$ group, a —$N^+R_{13}R_{14}R_{15}$ group, a ($C_3$-$C_7$)cycloalkyl group optionally substituted with a 5- or 6-membered aryl group, a 5- or 6-membered aryl group or a 5- to 12-membered heteroaryl group; said aryl or heteroaryl group being optionally substituted with one or more halogen atom, ($C_1$-$C_6$)alkyl group, ($C_1$-$C_4$)alkoxy group, or trifluoromethyl group;
$R_2$ represents a ($C_1$-$C_{10}$)alkyl group;
n is 1, 2, 3, 4 or 5;
$R_3$, $R_4$, $R_5$, $R_6$, $R_7$, $R_8$, $R_9$ and $R_{10}$ represent, independently of each other, a hydrogen atom, a halogen atom, —OH, —$N_3$, —$SCF_3$, a trifluoromethyl group, a ($C_1$-$C_6$) alkyl group, a ($C_1$-$C_6$)alkoxy group, a ($C_1$-$C_6$)alkyl-OH group, a —$NR_{11}R_{12}$ group, a —$N^+R_{13}R_{14}R_{15}$ group, a 5- or 6-membered aryl group or a 5- to 12-membered heteroaryl group;
$R_{11}$, $R_{12}$, $R_{13}$, $R_{14}$, and $R_{15}$ represent, independently of each other, a hydrogen atom or a ($C_1$-$C_6$)alkyl group;
$X^-$ is an anionic counterion, in particular chosen from $I^-$, $Cl^-$, $Br^-$, and $OH^-$.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

In the context of the present invention, the following definitions apply:
$C_t$-$C_z$: a carbon-based chain possibly containing from t to z carbon atoms in which t and z may take values from 1 to 10; for example, $C_1$-$C_6$ is a carbon-based chain possibly containing from 1 to 6 carbon atoms.
an alkyl: a linear or branched saturated aliphatic group, in particular comprising from 1 to 6 carbon atoms. Examples that may be mentioned include methyl, ethyl, n-propyl, isopropyl, n-butyl, isobutyl, tert-butyl, n-pentyl, etc. . . .

an alkenyl: a linear or branched unsaturated or partially unsaturated aliphatic group containing conjugated or non-conjugated double bond(s). Examples that may be mentioned include ethylenyl, propenyl, but-1-enyl, but-2-enyl . . .

an alkynyl: a linear or branched unsaturated or partially unsaturated aliphatic group containing conjugated or non-conjugated triple bond(s). Examples that may be mentioned include ethynyl, propynyl, but-1-ynyl, but-2-ynyl . . .

an alkoxy: a radical —O-alkyl in which the alkyl group is as defined previously.

a halogen atom: an atom chosen among Fluorine, Chlorine, Bromine, and Iodine.

a cycloalkyl group: a non aromatic mono- or bicyclic saturated or partially saturated or unsaturated ring containing 3 to 8 carbon atoms. Examples of cycloalkyl group that may be mentioned include cyclopropane, cyclobutane, cyclopentane, cyclopentene, cyclohexane or cyclohexene.

an aryl: a monocyclic or bicyclic aromatic group containing 5 or 6 carbon atoms. By way of examples of an aryl group, mention may be made of phenyl or naphthyl group. Preferably, the aryl group is phenyl.

a heteroaryl: a 5- to 12-membered monocyclic or bicyclic aromatic group containing from 1 to 5 heteroatoms chosen from O, S and N. Examples of monocyclic heteroaryls that may be mentioned include imidazolyl, pyrazolyl, thiazolyl, oxazolyl, isothiazolyl, isoxazolyl, furyl, thienyl, oxadiazolyl, thiadiazolyl, triazolyl, tetrazolyl, pyridinyl, pyrazinyl, pyrimidinyl, pyridazinyl and triazinyl. Examples of bicyclic heteroaryls that may be mentioned include indolyl, isoindolyl, benzofuryl, benzothiophenyl, benzoxazolyl, benzimidazolyl, indazolyl, benzothienyl, isobenzo furyl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl, pyrazolo[2,3-a]pyrazinyl, thiazolo[5,4-b]pyridyl, thiazolo[5,4-c]pyridyl, thiazolo[5,4-c]pyridyl, thiazolo[4,5-b]pyridyl, oxazolo[5,4-b]pyridyl, oxazolo[5,4-c]pyridyl, oxazolo[4,5-c]pyridyl, oxazolo[4,5-b]pyridyl, isothiazolo[5,4-b]pyridyl, isothiazolo[5,4-c]pyridyl, isothiazolo[4,5-c]pyridyl, isothiazolo[4,5-b]pyridyl, isoxazolo[5,4-b]pyridyl, isoxazolo[5,4-c]pyridyl, isoxazolo[4,5-c]pyridyl and isoxazolo[4,5-b]pyridyl. The heteroaryl groups may be more preferably chosen among quinolyl or pyridinyl groups.

According to a preferred embodiment, $R_1$ represents —OH, a $(C_1-C_6)$alkyl group, a $(C_2-C_6)$alkenyl group, or a $(C_3-C_7)$cycloalkyl group.

According to a preferred embodiment, $R_1$ represents —OH, a $(C_1-C_6)$alkyl group, or a $(C_3-C_7)$cycloalkyl group.

According to one embodiment, $R_1$ represents —OH. Advantageously, when $R_1$ represents —OH, n is 2.

According to another embodiment, $R_1$ represents a $(C_1-C_6)$alkyl group.

According to another embodiment, $R_1$ represents a $(C_3-C_7)$cycloalkyl group.

According to a preferred embodiment, $R_2$ represents a methyl group or an ethyl group.

According to one embodiment, $R_2$ represents a methyl group.

According to another embodiment, $R_2$ represents an ethyl group.

According to a preferred embodiment, n is 1 or 2.

According to one embodiment, n is 1.

According to another embodiment, n is 2.

Preferably, $R_3$, $R_4$, $R_5$, $R_6$, $R_7$, $R_8$, $R_9$ and $R_{10}$ are a hydrogen atom.

According to a preferred embodiment, the anionic counterion $X^-$ is an organic or inorganic anionic counterion, especially chosen from $I^-$, $Cl^-$, $Br^-$, and $OH^-$.

Preferably, the anionic counterion $X^-$ is chosen from $Br^-$, $I^-$ and $Cl^-$, and more preferably chosen from $I^-$ and $Cl^-$.

More preferably, the anionic counterion is $I^-$.

More preferably, the anionic counterion is $Cl^-$.

More preferably, the anionic counterion is $Br^-$.

It is clear that features of the above-mentioned embodiments may be combined with each other, unless specifically noted otherwise.

Among the compounds of general formula, mention may be made especially of the following compounds:

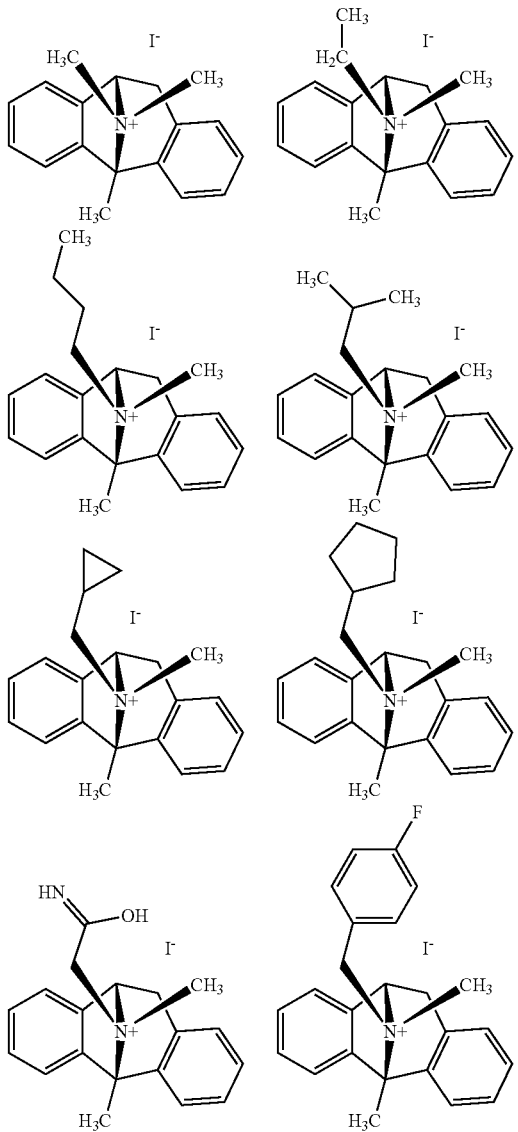

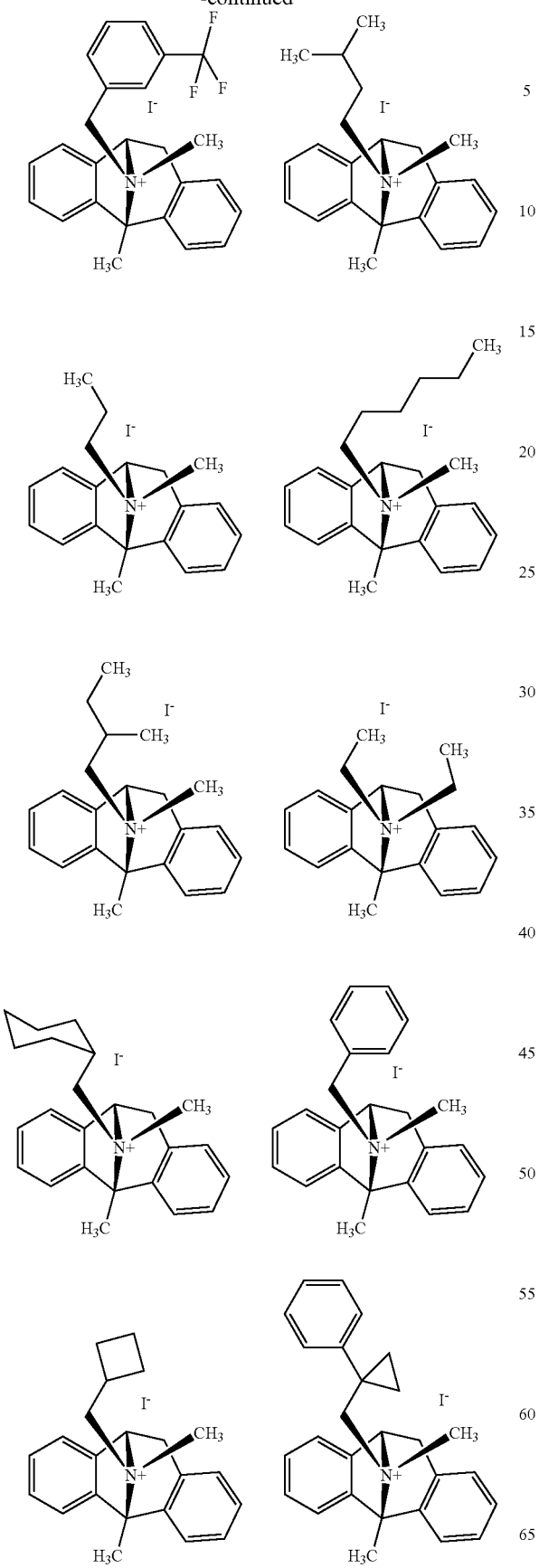
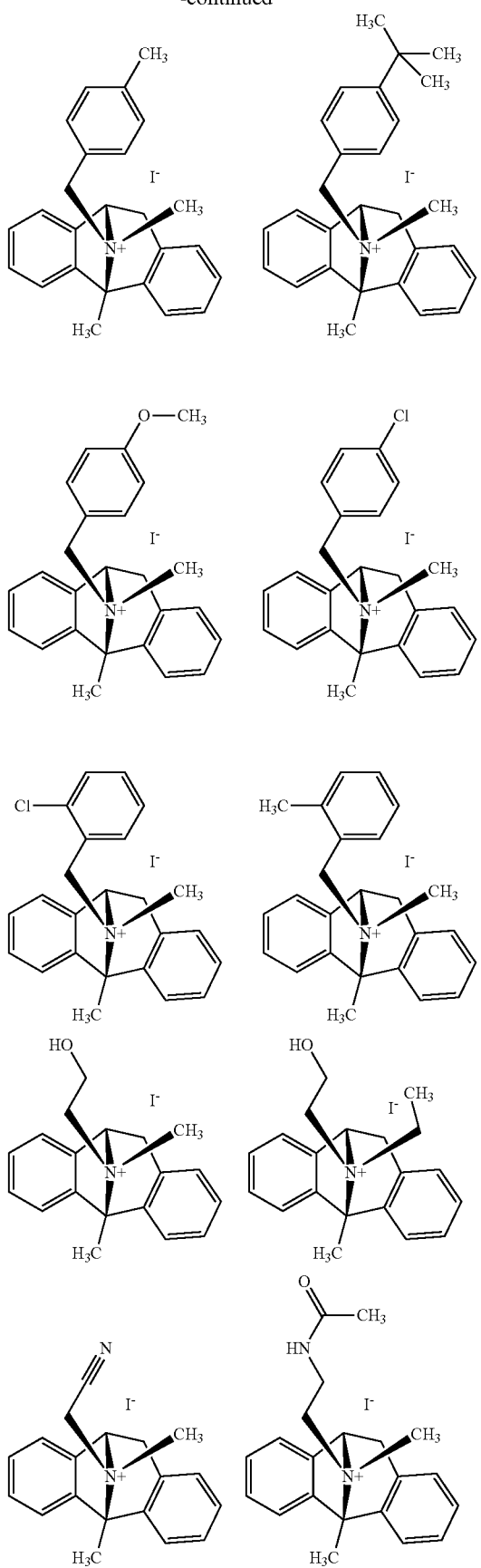

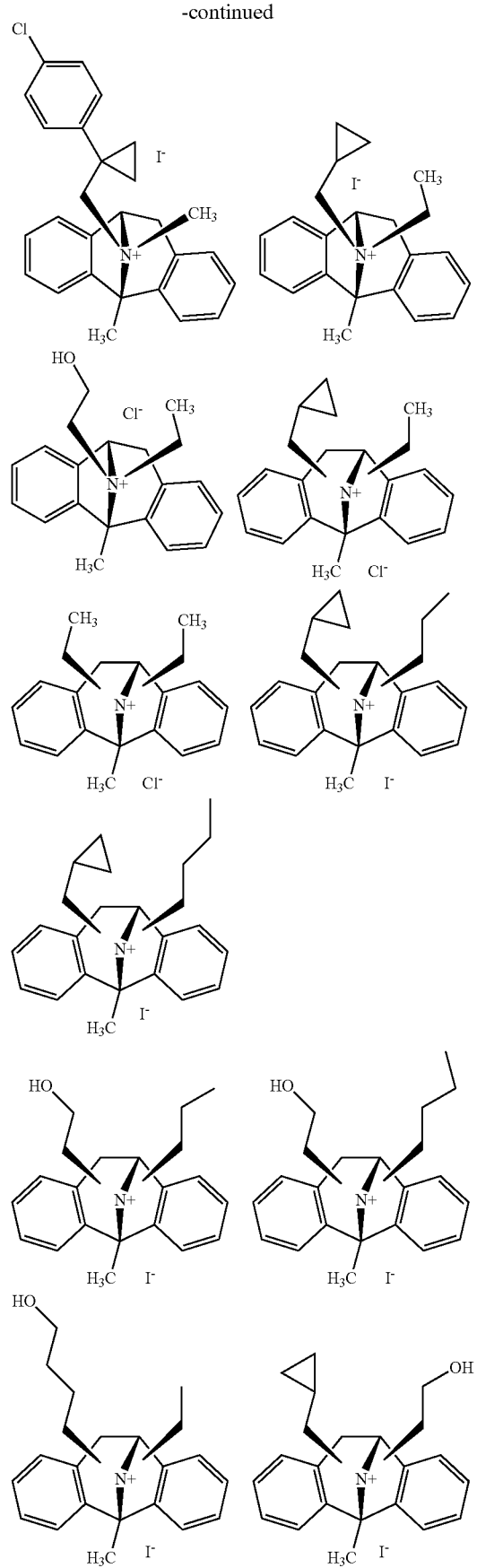
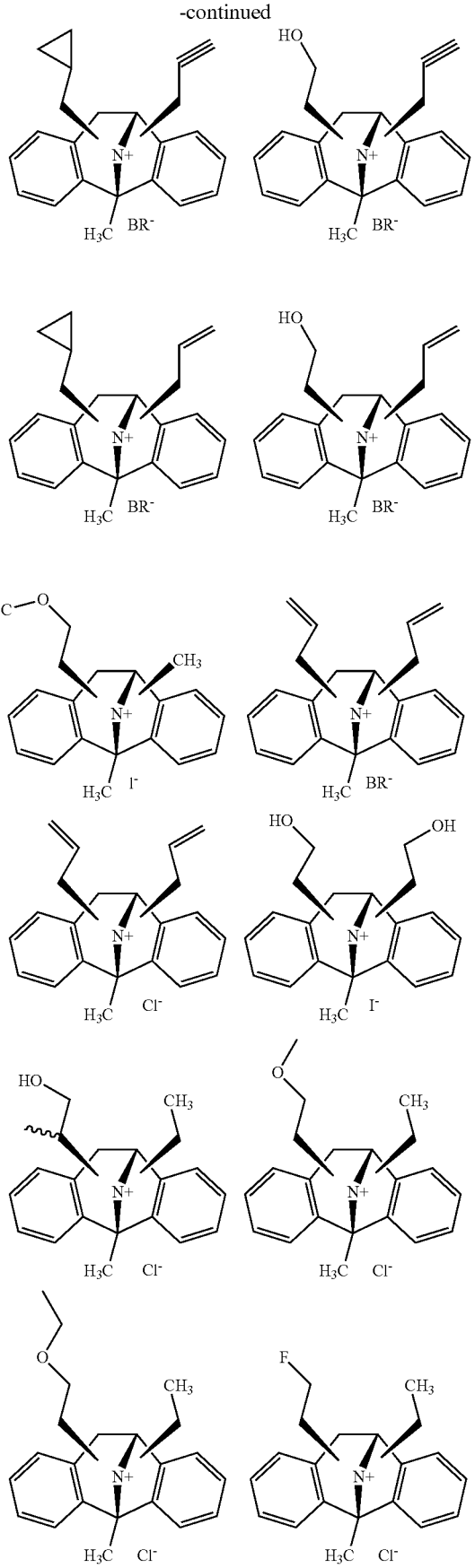

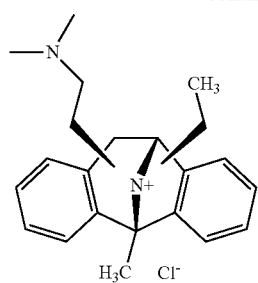
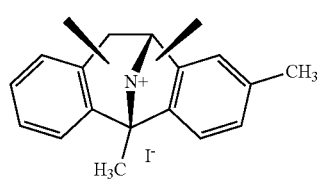
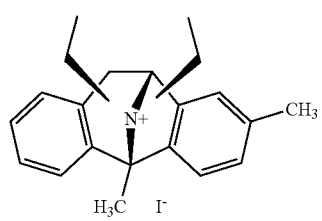
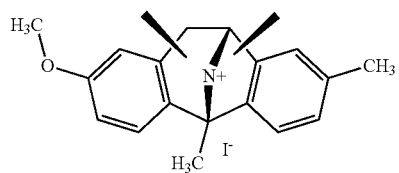
More preferably, among the compounds of general formula, mention may be made especially of the following compounds:
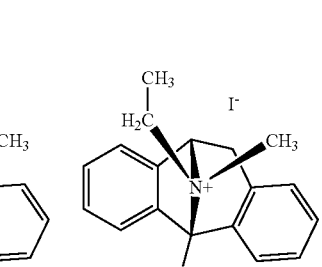
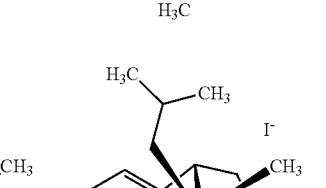
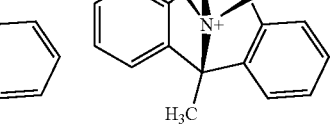
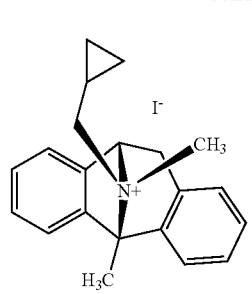
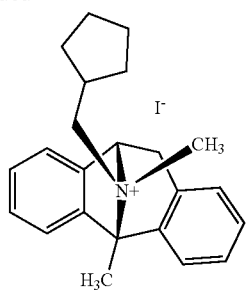
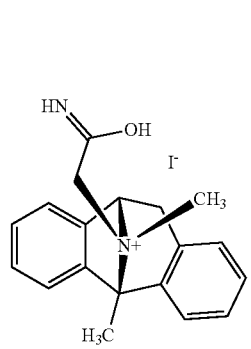
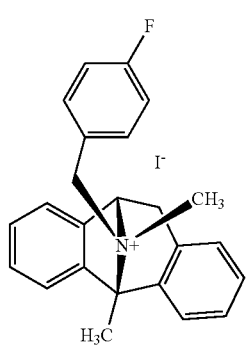
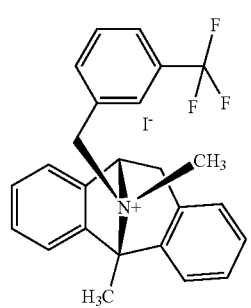
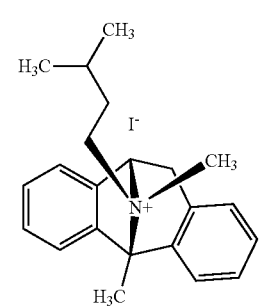
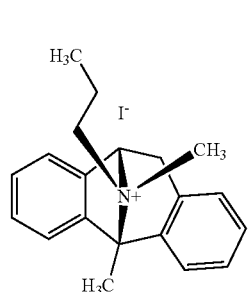
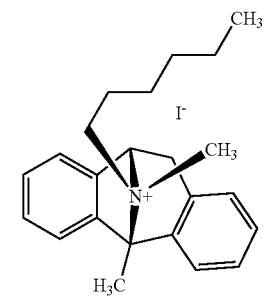

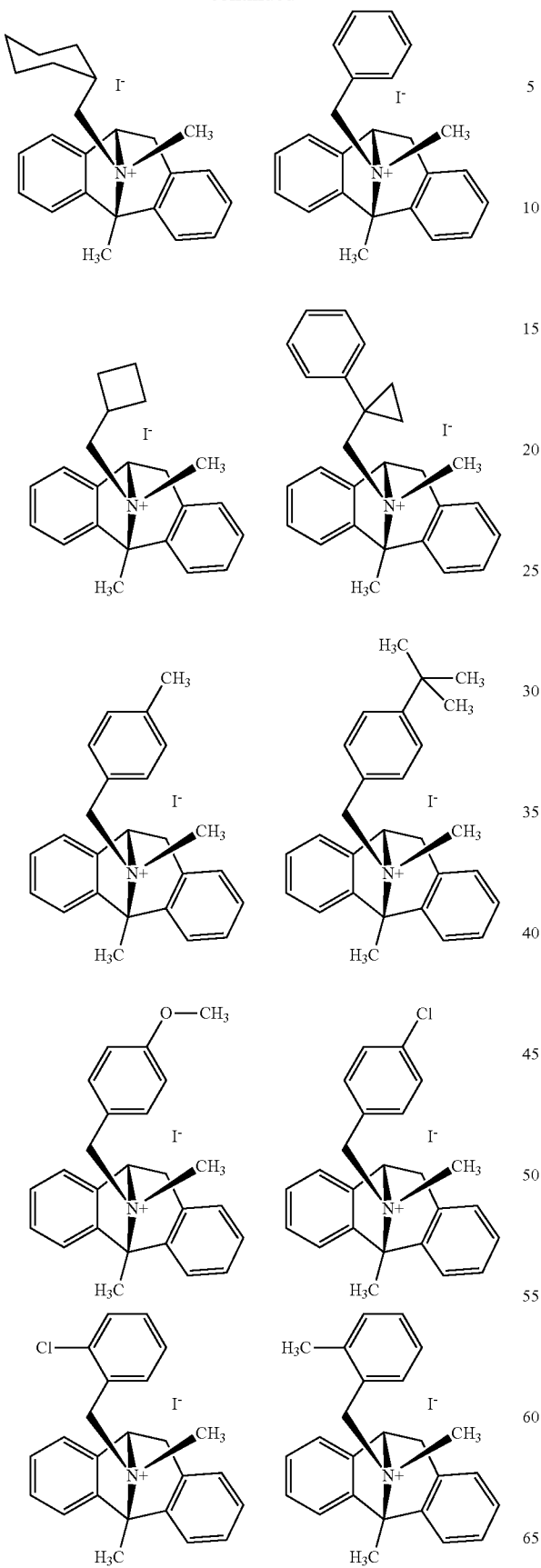
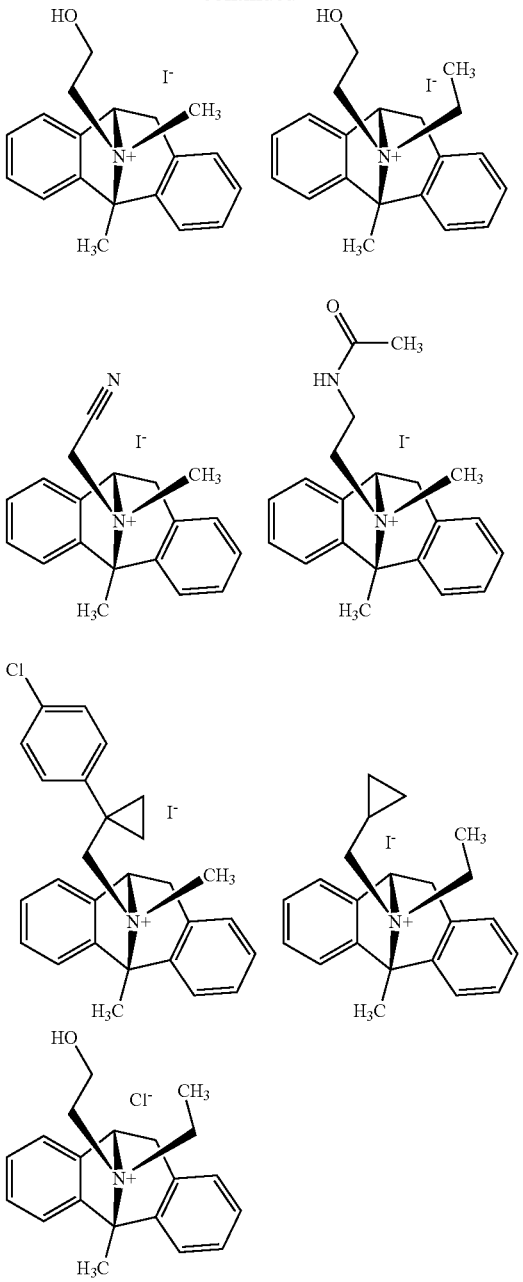
More preferably, among the compounds of general formula, mention may be made especially of the following compounds:
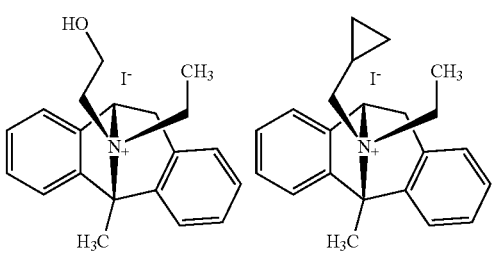

Preparation of the Compounds of the Invention

The compounds of the invention may be prepared according to methods well-known by the skilled artisan, as illustrated in the examples that follow.

According to a first embodiment, the synthesis of compounds of the present invention may be accomplished according to Scheme 1 below.

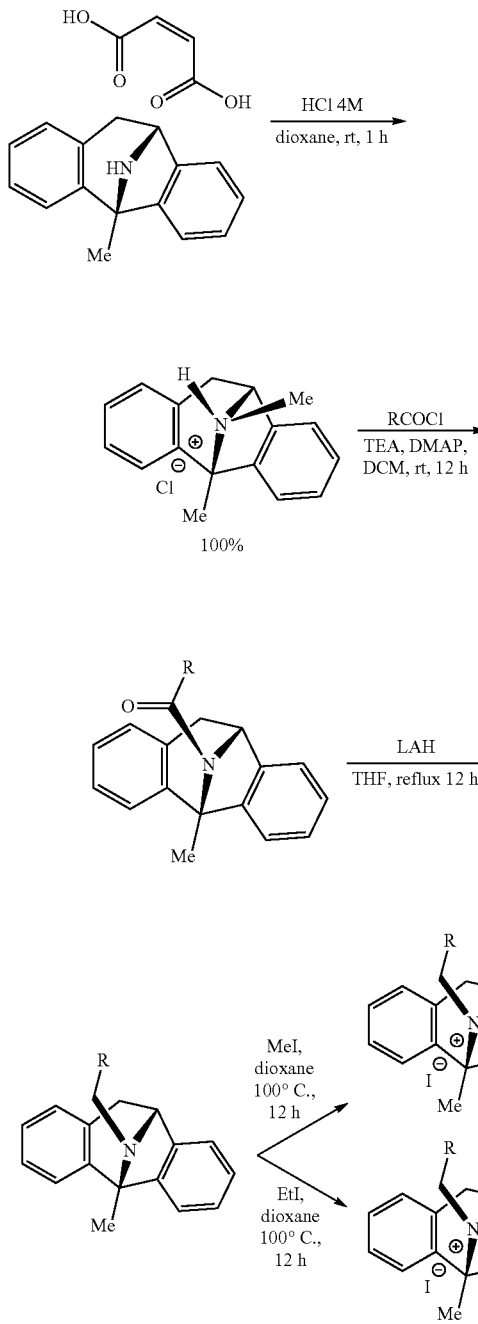

According to another embodiment, the synthesis of compounds of the present invention may be accomplished according to Scheme 2 below.

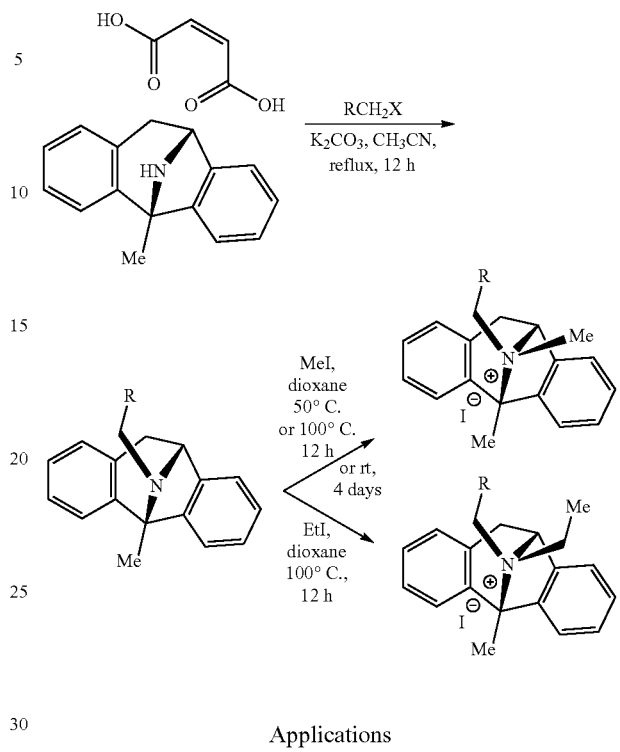

Applications

As specified previously and clearly illustrated by the following examples, the compounds according to the present invention are useful as peripheral NMDA receptor antagonists.

The present invention therefore provides a method for preventing and/or inhibiting and/or treating a disease or a condition in which the peripheral NMDA receptors are involved, comprising at least a step of administering to an individual in need thereof at least an effective amount of at least one compound in accordance with the invention.

In particular, the disease or the condition may be chosen among pulmonary hypertension, such as pulmonary arterial hypertension or thromboembolic pulmonary hypertension, pulmonary diseases involving inflammation, fibrosis and remodeling such as asthma, non-neuronal cancers such as colon, breast, lung or thyroid carcinoma, diabetes, atherosclerosis, sickle cell disease, diseases involving thrombosis, acute infections such as ARDS syndrome or ALI, chronic infectious diseases such as gastric ulcer induced by *Helicobacter pylori*, inflammatory/autoimmune diseases such as rheumatoid arthritis and irritable Bowel syndrome and osteoarthritis, heart failure, arrhythmias, renal disorders, pain, in particular peripheral neuropathic pain, psoriasis, atopic dermatitis and osteoporosis.

As mentioned above, pulmonary hypertension covers five groups of diseases.

The first group is pulmonary arterial hypertension. PAH may be associated with idiopathic and heritable PAH (bone morphogenetic protein receptor type 2 (BMPR2), ALK-1, Endoglin (ENG), SMAD9, Caveolin-1 (CAV1), KCNK3), with drug- and toxin-induced PAH, with connective tissue diseases, with human immunodeficiency virus, with portal hypertension, with congenital heart diseases, with schistosomiasis, with pulmonary veno-occlusive disease, pulmonary capillary hemangiomatosis, and persistent PH of the newborn.

The second group is PH due to left heart disease. It encompasses the most frequent form of PH, i.e. left ventricular systolic dysfunction, left ventricular diastolic dysfunction, valvular disease and congenital/acquired left heart inflow/outflow tract obstruction and congenital cardiomyopathies.

The third group is PH due to lung diseases and/or hypoxia. This group comprises patients with parenchymal lung diseases or other causes of hypoxia in whom the presence of PH is considered directly related to these underlying diseases. More particularly, it comprises chronic obstructive pulmonary disease, interstitial lung disease, other pulmonary diseases with mixed restrictive and obstructive pattern, sleep-disordered breathing, alveolar hypoventilation disorders, chronic exposure to high altitude and development lung diseases.

The fourth group is chronic thromboembolic pulmonary hypertension.

The fifth group is PH with unclear or multifactorial mechanisms. Included in this group are numerous forms of PH in which multiple pathophysiological mechanisms might be implicated in the elevation in pulmonary vascular pressures. It encompasses hematologic disorders (chronic haemolytic anemia, myelo-proliferative disorders, splenectomy), systemic disorders (sarcoidosis, pulmonary histiocytosis, lymphangioleiomyomatosis), metabolic disorders (glycogen storage disease, Gaucher disease, thyroid disorders) and others such as tumoral obstruction, fibrosing mediastinitis, chronic renal failure and segmental PH.

Of course, this recent classification is constantly evolving, and new groups and/or subgroups, also covered in the context of the present invention, are regularly discovered.

More specifically, according to the present invention, the disease or the condition is pulmonary hypertension, such as pulmonary arterial hypertension or thromboembolic pulmonary hypertension, and preferably pulmonary arterial hypertension.

The compounds according to the invention may be used for the preparation of medicaments.

Thus, according to yet another of its aspects, the present invention relates to a medicament comprising as pharmaceutical active agent at least one compound according to the invention.

In other words, the present invention relates to a compound according to the invention for use as a medicament.

According to another of its aspects, the present invention relates to a pharmaceutical composition comprising at least one compound according to the invention, and at least one pharmaceutically acceptable excipient.

According to one embodiment, a pharmaceutical composition of the invention may be intended to be administered separately, sequentially or simultaneously with an agent useful for the prevention and/or the inhibition and/or the treatment of a disease condition, said agent being different from the compound of formula (I) of the invention.

Thus, the present invention also relates to a pharmaceutical composition comprising at least one compound according to the invention in combination with at least one other therapeutic agent, and at least one pharmaceutically acceptable excipient.

According to one embodiment, the compounds of the present invention may be used alone or combined with one other therapeutic agent, for example vasodilator agents, other glutamate receptor antagonists (ionotropic and/or metabotropic), and in particular other NMDAR antagonists, chemotherapeutic agents, other pulmonary hypertension regimen or radiotherapeutic regimen and their mixtures.

Preferably, the present invention relates to a pharmaceutical composition comprising at least one compound according to the invention in combination with at least one other therapeutic agent, and preferably with vasodilator agents and/or other glutamate receptor antagonists (ionotropic and/or metabotropic), and in particular other NMDAR antagonists.

In the meaning of the present invention, "glutamate receptor antagonists" comprises two families: ionotropic (ion channels) and metabotropic (receptors with seven transmembrane domains). Among ionotropic, there are NMDAR, AMPA and Kainates. Ionotropic and metabotropic families are more particularly defined in the Guide to Pharmacology (IUPHAR/BPS).

Thus, according to one embodiment, a method of the invention may comprise the step of administering a compound of formula (I) in accordance with the invention, separately, sequentially or simultaneously with another therapeutic agent, and preferably with vasodilator agents and/or other glutamate receptor antagonists (ionotropic and/or metabotropic), and in particular NMDAR antagonists.

With respect to the use of the claimed compounds, in particular for treating pulmonary hypertension, it may be particularly advantageous to combine them with another or several others conventional therapeutic active(s) already considered in the treatment of such diseases. Since the claimed compounds acts according a specific new route, it may be expected to achieve a better result by simultaneously acting through different therapeutic routes.

In particular, this embodiment may allow reducing the therapeutic doses of respective compounds of the present invention, to administrate to the patient, thus allowing less adverse effects. In addition, this embodiment allows achieving additive or synergistic effect of the respective combined compounds of the present invention.

Thus, the present invention is also directed to a method of treatment of pulmonary hypertension, and in particular pulmonary arterial hypertension, comprising the administration of a claimed compound, advantageously combined with the administration of at least one active agent selected among the group consisting of vasodilator agents, other glutamate receptor antagonists (ionotropic and/or metabotropic), and in particular other NMDAR antagonists, chemotherapeutic agents, other pulmonary hypertension regimen or radiotherapeutic regimen and their mixtures.

For example, the compounds of the present invention may be used combined with endothelin receptor antagonists (ERAs), such as bosentan (Tracleer™, Actelion) and ambrisentan (Letairis™, Gilead), prostacyclin derivatives such as epoprostenol (Flolan™, Gsk, Actelion), treprostinil (Remodulin™, United Therapeutics) and Iloprost™ (Actelion), or PDE5 inhibitors such as Sildenafil (Revatio™, Pfizer) and Tadalafil (Adcirca™, Lilly).

As examples of chemotherapeutic agents that may be suitable for the invention, one may mention chemotherapeutic agents chosen from alkylating agents, intercalating agents, antimicrotubule agents, antimitotics, antimetabolites, antiproliferative agents, antibiotics, immunomodulatory agents, anti-inflammatories, kinases inhibitors, antiangiogenic agents, antivascular agents, oestrogenic and androgenic hormones.

A radiotherapeutic regimen may be administrated by exposing an individual in need thereof to a source of ionizing radiation such as X-ray, gamma-ray or beta-ray.

The pharmaceutical compositions may contain more particularly an effective dose of at least one compound according to the invention.

An "effective dose" means an amount sufficient to induce a positive modification in the condition to be regulated or treated, but low enough to avoid serious side effects. An effective amount may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound of formula (I) according to the invention may be administered in an effective dose by any of the accepted modes of administration in the art.

In one embodiment, a compound of the invention may be used in a composition intended to be administered by oral, nasal, sublingual, aural, ophthalmic, topical, rectal, vaginal, urethral, or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

The present invention will be better understood by referring to the following examples and figures which are provided for illustrative purpose only and should not be interpreted as limiting in any manner the instant invention.

FIGURES

FIG. 1: Effect of NMDAR knockout in smooth muscle cells on the development of pulmonary hypertension. NMDAR knockout in smooth muscle cells attenuates hemodynamic and cardiac parameters of pulmonary hypertension as assessed by measurement of right ventricular systolic pressure and Fulton index. Right ventricular systolic pressure (RVSP) measurement in wild-type mice (n=8-14) and mice with a knockout of NMDAR in SMCs (n=7-13) after 3 weeks of normoxia or chronic hypoxia ($FiO_2$: 10%). Ratio of right ventricle weight to left ventricle plus septum weight (Fulton index) for wild-type mice (n=12) and mice with a knockout of NMDAR in SMCs (n=8-12) after 3 weeks of normoxia or chronic hypoxia ($FiO_2$:10%).

Figure 2:
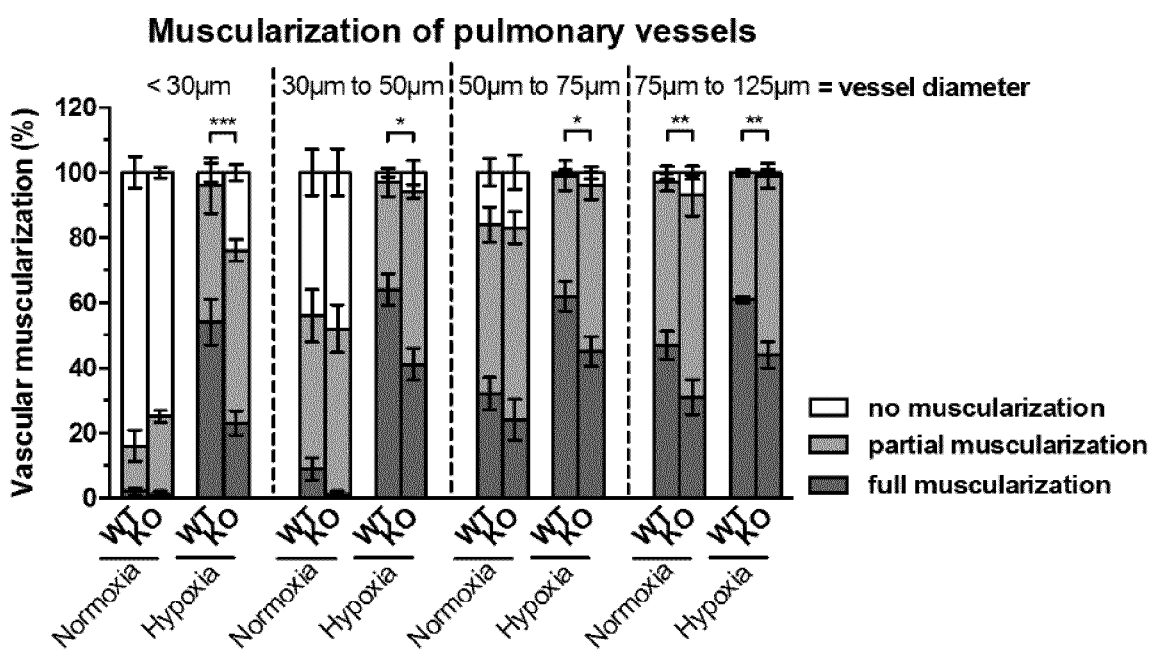

FIG. 2: Effect of NMDAR knockout in smooth muscle cells on the development of pulmonary hypertension. NMDAR knockout in smooth muscle cells attenuates vascular remodeling of pulmonary hypertension as assessed by morphometric analysis. Morphometric analysis of pulmonary vessels in wild-type mice (n=5) and mice with a knockout of NMDAR in SMCs (n=5) after 3 weeks of normoxia or chronic hypoxia (FiO2: 10%). Same experiment as in FIG. 1. Pulmonary vessels were assigned to four groups on the basis of external vessel diameter (<30 μm, 30 μm to 50 μm, 50 μm to 75 μm and 75 μm to 125 μm). Each vessel was classified as non-muscularized (VWF+, α-smooth muscle actin-), partially muscularized (VWF+, α-smooth muscle actin+/−), or fully muscularized (VWF+, α-smooth muscle actin+). Statistical significance was determined by a Mann-Whitney test (a), regular two-way ANOVA followed by Bonferonni's tests (b-d), a one-way ANOVA followed by Bonferroni's multiple comparison tests (e). *P<0.05, P<0.01, *P<0.001 versus WT/control (a-d) or §§§ P<0.001 versus control, ***P<0.001 versus PDGF (e). The values shown are means±SEM (a-e).

Figure 3:
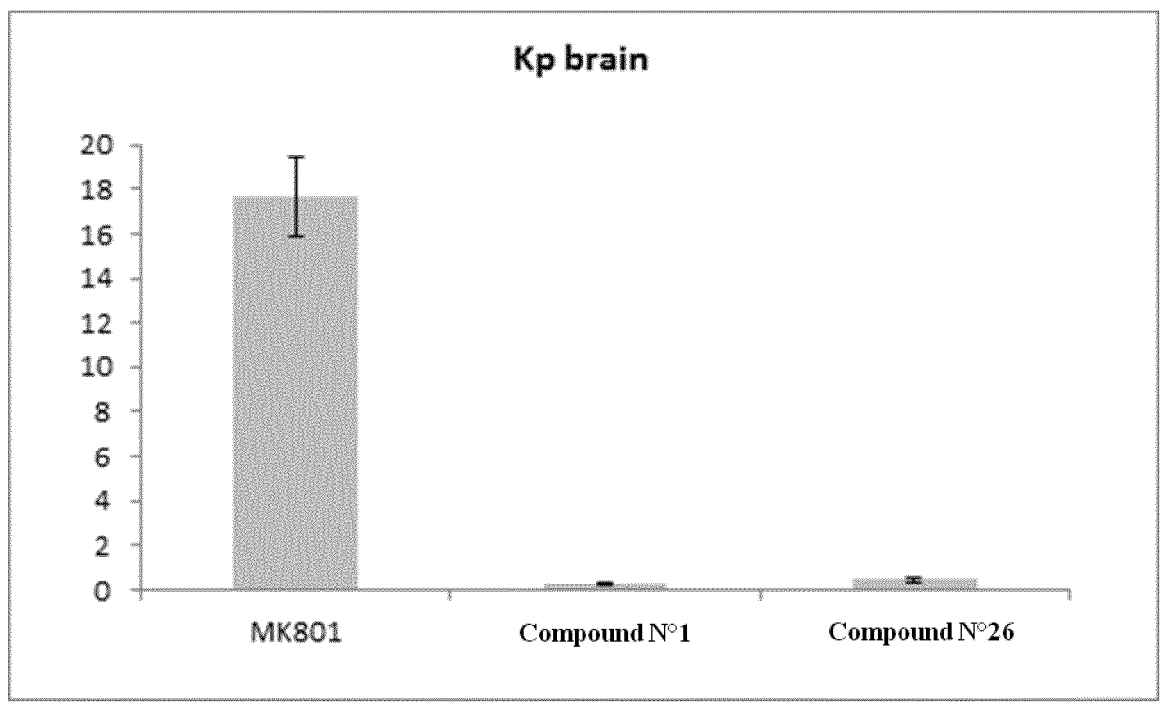

FIG. 3: Measures of brain/plasma ratio ($Kp_{"brain"}$) of MK801, Compound No 1 and Compound No 26 in rat. The results are expressed as the mean values obtained from 3 rats for each compound. Bars represent standard deviations. $Kp_{"brain"}$ MK-801=17.7±1.75. $Kp_{"brain"}$ Compound No 1=0.3±0.03. $Kp_{"brain"}$ Compound No 26=0.4±0.08.

EXAMPLES

Methods

Animal Models of Pulmonary Hypertension

All animals were used in strict accordance to the European Union regulations (Directive 2010/63/UE) for animal experiments. All animals were maintained in a temperature and humidity-controlled room with a 12 hours/12 hours light/dark cycle with access to a standard chow and water ad libitum.

Following procedures performed on mice, were approved by the ethical committee CEEA26 (Animal experimentation ethic committee No 26) and the French ministry of higher education and research.

Transgenic mice strains used are B6.129S4-Grin1tm2Stl/J (further named as GRIN1fl/fl mice), B6.129S6-Taglntm2 (cre)Yec/J (further named as Tagln-cre mice) (both from JACKSON LABORATORY) and B6.Cg-Tg(Tek-cre/ERT2) 1Arnd/ArndCnrm (further named as Tek-cre mice) (EUROPEAN MOUSE MUTANT ARCHIVE).

Briefly, GRIN1fl/fl mice were crossed with either Tek-cre mice or tagln-cre mice. For NMDAR knocked out in smooth muscle cells, experiments were performed on male Tagln-cre×GRIN1fl/fl mice and male Tagln-cre mice were used as controls. For NMDAR knocked out in endothelial cells, experiments were performed on male Tek-cre×GRIN1fl/fl mice and male Tek-cre mice were used as controls after 5 weeks of Tamoxifen-containing chow (HARLAN LABORATORIES) administration followed by 1 week of standard chow. In both experiments, pulmonary hypertension was induced exposing mice to 3 weeks of hypoxia (10% $FiO_2$). Then, mice were submitted to anesthesia induced by inhalation of isoflurane 3% mixed with air and maintained decreasing isoflurane concentration between 1% and 1.5%. The heart was taken out the thoracic cage, auricles were removed and right ventricles were separated from left ventricles associated to septa. The weight of each part was measured and the ratio of the right ventricle weigh to the left ventricle with septum weigh was calculated for each mouse. Lungs were processed inflating them with 10 mL of a mixture of saline and OCT 1/1 ratio (ShandonTMCryomatrix™, THERMOFISCHER SCIENTIFIC). Ventricles and inflated lungs were then frozen in cooled isopentane (VWR) and stored at −80° C.

Morphometric Analysis

6 μm thick sections of mouse lungs were cut with a cryomicrotome (LEICA MICROSYSTEMS). Sections were allowed to dry during 1 hour under a hood. Then, they were fixed in cold acetone for 10 minutes. 10% goat serum plus 5% mouse serum were incubated for 1 hour to prevent unspecific binding of antibodies. Anti-VWF and Anti-alpha smooth muscle cell-FITC antibodies were incubated in presence of 2% mouse serum during 1 hour at room temperature. A negative control was performed omitting primary antibodies. The secondary antibody was incubated during 30 minutes in presence of 2% mouse serum. DAPI (LIFE TECHNOLOGIES) diluted at 1/500 was incubated during 1 minute. Glass slides were finally mounted using Dako Fluorescent mounting medium (DAKO). Sections were then analyzed using Eclipse 80i microscope coupled to Nis Elements BR2.30 software (NIKON).

For morphometric analysis performed on mouse lungs, intrapulmonary arterioles were divided in four groups based on their external diameter: less than 30 μm, from 30 μm to 50 μm, from 50 μm to 75 μm and from 75 μm to 125 μm. 20 arterioles per category identified with the VWF staining were qualified as non muscularized, partially muscularized or fully muscularized based on the alpha smooth muscle actin staining. 5 mice/group were included in the study.

In Vivo Brain Penetration Measurement: Drug Administration and Sampling of Brain and Plasma The femoral vein of male Sprague-Dawley rats (CRL) weighing around 250 g was surgically catheterized at least 72 hours prior to the experiment. 3 animals were performed for each compound tested. The drug was administered as 3.45 h constant-rate intravenous infusion to approach steady state, using a flow rate of 0.8 mL/h, corresponding to dosage of 4 mg/kg (1.067 mg/kg/h, i.e. 1 mg/rat of ~250 g). The vehicle used was saline.

At the end of the infusion, the rats were anesthetized by inhalation of isoflurane, and blood was collected in a heparinized tube from the abdominal aorta, followed by immediate rinsing of the bloodstream for 2 minutes with saline at a rate of 15 mL/min using a peristaltic pump and left intraventricle cannula (flowing via right atrium). The brain (without cerebellum) was removed, and transferred in a tube and homogenized in two volumes of deionized water using a tissue homogenizer (Precellys24). All samples were stored at −20° C. until analysis. Plasma and brain homogenate sample preparation was performed using solid phase extraction on OASIS® WCX (Waters) and compounds were quantified by reversed phase liquid chromatography and positive electrospray ionization and multiple reaction monitoring mass spectrometry (LC-MS/MS).

Cultures of Hippocampal Neurons

For hippocampal neurons isolation and culture, all animals were used in strict accordance to the European Union regulations (Directive 2010/63/UE) for animal experiments. 18 day-pregnant female Wistar rats were decapitated, and fetuses were rapidly extracted from uterus and transferred in dissection solution (50 ml PBS (LIFE TECHNOLOGIES)+ 50 units/ml penicillin-streptomycin (Abx) (THERMOFISCHER SCIENTIFIC)+0.6% glucose. The rat fetus brains were quickly removed and placed in dissection solution before hippocampus extraction. Hippocampus were collected in HBSS (43.5 ml PBS, 0.6% glucose, 100 mM HEPES (LIFE TECHNOLOGIES), 100 units/ml Abx) and digested by addition of 0.25% trypsin (LIFE TECHNOLOGIES) and 0.1% DNAse I. After 10 minutes incubation at 37° C., 10% FBS (THERMOFISCHER SCIENTIFIC) was added to stop digestion. Cells were then mechanically dissociated by gentle pipetting to obtain uniform suspension. After centrifugation (10 minutes, 100 G) supernatant was removed and cell pellet was suspended in HC medium (50 ml neurobasal medium, 1 ml B27 supplement, 500 μl glutamine 200 mM 100× (all from LIFE TECHNOLOGIES), 50 units/ml Abx) plus 10% FBS and without Abx. Cells were counted and 630,000 cells were dispatched in each poly-D-lysine-coated 35 mm petri dishes (BD Falcon, CORNING) containing 2 ml HC for culture. After 6 days of culture, cytosine 13-D-arabinofuranoside (Ara-C) was added to inhibit proliferation of glial cells. Cells were then used from DIV 14. Cells were cultured at 37° C. in a humidified atmosphere of 5% $CO_2$ and 95% air.

Electrophysiology

Chemicals used for patch-clamp solutions were provided by Sigma-Aldrich. TTX was provided by R&D, CNQX by Abcam. Whole-cell voltage clamp recordings from rat hippocampal neurons were made with patch pipettes (5-6 MΩ) filled with intracellular solution (in mM): 150 CsCl, 5 EGTA, 10 HEPES; its pH was adjusted to 7.2 with NaOH. The external bath solution contained (in mM): 140 NaCl, 3 KCl, 2 $CaCl_2$, 10 HEPES, 10 glucose, 0.5 μM TTX, 20 μM picrotoxin and 20 μM CNQX; its pH was adjusted to 7.4 with CsOH. The membrane potential was clamped at −60 mV. Currents were monitored using an AxoPatch200B patch clamp amplifier (Axon Instruments, Sunnyvale, Calif., USA) filtered at 2 kHz and digitized at 100 Hz. Experiments were controlled by data acquisition board (National Instruments). Data were analyzed by Exel and GraphPad software. Liquid junction potentials were measured with the patch clamp amplifier. Transmembrane currents were evoked in acutely isolated neurons by the application of 100 μM NMDA and 20 μM D-serine. Antagonists of NMDA receptors were applied at increasing concentration. Cells were constantly perfused using gravity-fed bath at 1-2 ml/min. To calculate the percentage block by antagonist, residual desensitization of NMDA-induced currents was compensated by fitting exponentials to the pre-antagonist portion of traces.

Statistical Analysis

Results are expressed as mean+SEM of measurement unless otherwise indicated. Gaussian distribution of all data was assessed using Kolmogorov-Smirnov test or Shapiro-Wilk depending on sample size. To compare two groups of data, either unpaired t test or Mann-Whitney test were used depending on the data distribution. For multiple comparisons, one-way analysis of variance followed by Bonferroni test or Kruskal-Wallis followed by Dunn's tests were used when it was appropriate. Results from transgenic mice were analyzed with a two-way analysis of variance followed by a Bonferroni test. Differences were considered significant with a P value<0.05. Statistical analysis was performed with Prism 6 (GRAPHPAD SOFTWARE) and Excel softwares.

Example 1

Preparation of the Compounds According to the Invention

In accordance with the invention, the preparation of compounds of general formula (I) is illustrated below.

General Procedure A for the Preparation of 1-((5S, 10R)-5-methyl-10,11-dihydro-5H-5,10-epiminodibenzo[a,d][7]annulen-12-yl)ketone To a solution of 258 mg of MK801 hydrochloride (1 mmol) in 10 mL of dry DCM were added 1.5 equivalent of the corresponding acyl chloride, 20 mol % of DMAP and 3 equivalent of TEA under argon. The mixture was stirred at room temperature for 12 hours to 20 hours (reaction monitored by TLC). 50 mL of diethyl ether was added to the reaction mixture. The solution obtained was washed two times with 15 mL of saturated aqueous solution of $NH_4Cl$. Organic layers were dried over sodium sulfate, concentrated under reduce pressure, at 10 mbar, and the crude product was purified by column chromatography on silica gel.

General Procedure B for Reduction of 1-((5S,10R)-5-methyl-10,11-dihydro-5H-5,10-epiminodibenzo[a,d][7]annulen-12-yl)ketone To 1 equivalent of a solution of MK801 amide derivative in 0.2 M of anhydrous THF was added 5 equivalent of $LiAlH_4$ under argon atmosphere at 0° C. After stirring at room temperature for an additional period of 30 minutes, the mixture was heated at reflux for 12 hours to 24 hours (reaction monitored by TLC). After being allowed to cool to room temperature, the mixture was treated with drop-to-drop addition of water at 0° C. till complete destruction of excess LAH. The mixture was then filtered on celite pad, washed with diethyl ether and the resultant solution was washed with brine. After drying over sodium sulfate, evaporation of the solvent under reduced pressure, at 10 mbar, the amine was directly engaged in the next step without purification.

General Procedure C for Preparation of (5S,10R)-12-$CH_2$R-5-methyl-10,11-dihydro-5H-5,10-epiminodibenzo[a,d][7]annulene To 1 equivalent of a solution of MK801 maleate in 0.1 M of anhydrous acetonitrile were added 3.5 equivalent of $K_2CO_3$ and 1.1 equivalent of $RCH_2X$ under argon atmosphere, at room temperature. After stirring at reflux for 12 hours (reaction monitored by TLC), and after being allowed to cool to room temperature, the mixture was filtered on celite pad and washed with ethyl acetate. After evaporation of the solvents under reduced pressure, at 10 mbar, the amine was directly engaged in the next step without purification.

General Procedure D for Quaternarization of (5S,10R)-12-$CH_2$R-5-methyl-10,11-dihydro-5H-5,10-epiminodibenzo[a,d][7]annulene To a solution of 1 equivalent of the corresponding amine in 0.2 M of dioxane in a microwave-type tube, was added 80 equivalent of alkyl iodide. The vial is sealed, and the mixture was heated at 50° C. or 100° C. under stirring for 12 hours/or stirred at room temperature for four days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure, at 10 mbar, to give the desired quaternarized ammonium iodide salt, eventually purified over preparative plate.

Compound No 1

Compound No 1 is prepared according to the general procedure D.

To a solution of 674 mg of (+)-MK801 maleate (2 mmol) in 5 mL of dioxane were added 2.59 g of cesium carbonate (8 mmol) and 5 mL of methyl iodide (80.3 mmol) to give 720 mg of Compound No 1 as a white solid without purification.

Yield: 98%.

Melting point=270-280° C.

$^1$H NMR δ (300 MHz, $CDCl_3$) (ppm): 7.52 (br d, J=6.9 Hz, 1H), 7.41-7.27 (m, 5H), 7.15-7.09 (m, 2H), 6.37 (d, J=5.0 Hz, 1H), 3.99 (dd, J=18.8 Hz, 5.9 Hz, 1H), 3.55 (s, 3H), 3.44 (s, 3H), 3.11 (d, J=18.8 Hz, 1H), 2.19 (s, 3H).

$^{13}$C NMR δ (75 MHz, MeOH d4) (ppm): 144.8, 137.4, 136.1, 131.5, 131.2 (2C), 131.0, 130.6, 129.3, 125.1, 124.9, 122.2, 82.8, 75.9, 42.7, 32.4 (2C), 12.6.

IR (neat) ($cm^{-1}$): $\lambda_{max}$=3462, 3042, 3007, 2949, 1612, 1478, 1461, 1429, 1391, 1318, 1262, 1237, 1167, 1084, 1006, 971, 932, 809, 787, 768, 718.

HRMS (ESI positive):

Calculated for $C_{18}H_{20}N$ $[M-I]^+$ 250.1596; Found 250.1592.

$[\alpha]_D^{20}$+190° (c 0.50, MeOH).

Compound No 2

Compound No 2 is prepared according to the general procedure D.

To a solution of 122 mg of (5S,10R)-12-ethyl-5-methyl-10,11-dihydro-5H-5,10-epiminodibenzo[a,d][7]annulene (0.5 mmol) in 2 mL of dioxane were added 2.5 mL of methyl iodide (40.2 mmol) to give 128 mg of Compound No 2 as a white solid without purification.

Yield: 64%.

Melting point=230-232° C.

$^1$H NMR δ (300 MHz, $CDCl_3$) (ppm): 7.7-7.63 (m, 1H), 7.41-7.35 (m, 1H), 7.35-7.23 (m, 4H), 7.14-7.06 (m, 2H), 6.07 (d, J=5.3 Hz, 1H), 3.77-3.6 (m, 2H), 3.5-3.36 (m, 1H), 3.29 (s, 3H), 3.15 (d, J=19.0 Hz, 1H), 2.26 (s, 3H), 1.65 (t, J=7.2 Hz, 3H).

$^{13}$C NMR δ (75 MHz, $CDCl_3$) (ppm): 143.2, 135.2, 134.4, 130.4, 130.1, 130.0 (2C), 129.2, 128.4, 124.4, 123.8, 120.6, 82.7, 71.2, 49.7, 45.9, 31.6, 14.1, 10.5.

IR (neat) ($cm^{-1}$): $\lambda_{max}$=3462, 3010, 2944, 2839, 1613, 1478, 1452, 1425, 1398, 1307, 1275, 1252, 1132, 1088, 1042, 1028, 965, 903, 811, 768, 751, 667.

HRMS (ESI positive):

Calculated for $C_{19}H_{22}N$ $[M-I]^+$ 264.1752; Found 264.1749.

$[\alpha]_D^{20}$+178° (c 0.50, MeOH).

Compound No 3

Compound No 3 is prepared according to the general procedure D.

To a solution of 70 mg of (5S,10R)-12-butyl-5-methyl-10,11-dihydro-5H-5,10-epiminodibenzo[a,d][7]annulene (0.25 mmol) in 1 mL of dioxane were added 1.25 mL of methyl iodide (20 mmol) to give 104 mg of Compound No 3 as a yellow solid without purification.

Melting point=200-203° C.

$^1$H NMR δ (300 MHz, $CDCl_3$) (ppm): 7.69-7.63 (m, 1H), 7.39-7.33 (m, 1H), 7.33-7.21 (m, 4H), 7.12-7.04 (m, 2H), 6.04 (d, J=5.2 Hz, 1H), 3.67-3.46 (m, 2H), 3.29 (s, 3H), 3.28-3.20 (m, 1H), 3.15 (d, J=18.7 Hz, 1H), 2.25 (s, 3H), 2.14-1.96 (m, 2H), 1.48-1.18 (m, 2H), 0.9 (t, J=7.4 Hz, 3H).

$^{13}$C NMR δ (75 MHz, $CDCl_3$) (ppm): 143.1, 135.3, 134.4, 130.29, 130.22, 130.1 (2C), 129.2, 128.4, 124.5, 123.8, 120.6, 82.9, 71.6, 54.1, 46.5, 31.7, 26.1, 20.4, 14.1, 13.8.

IR (neat) ($cm^{-1}$): $\lambda_{max}$=3467, 3008, 2960, 2932, 2873, 1612, 1479, 1461, 1425, 1395, 1275, 1233, 1159, 1083, 1059, 1042, 917, 897, 810, 786, 767, 677.

HRMS (ESI positive):

Calculated for $C_{21}H_{26}N$ $[M-I]^+$ 292.2065; Found 292.2061.

$[\alpha]_D^{20}$+151° (c 0.5, MeOH).

Compound No 4

Compound No 4 is prepared according to the general procedure D.

To a solution of 85 mg of (5S,10R)-12-isobutyl-5-methyl-10,11-dihydro-5H-5,10-epiminodibenzo[a,d][7]annulene (0.3 mmol) in 1.5 mL of dioxane were added 1.5 mL of methyl iodide (24.1 mmol) to give 100 mg of Compound No 4 as a white solid without purification.

Yield=75%.

Melting point=216-217° C.

$^1$H NMR δ (300 MHz, CDCl$_3$) (ppm): 7.70 (br d, J=6.9 Hz, 1H), 7.37-7.31 (m, 1H), 7.31-7.20 (m, 4H), 7.11-7.02 (m, 2H), 6.22 (d, J=5.2 Hz, 1H), 3.60 (dd, J=18.5 Hz, 5.4 Hz, 1H), 3.30 (s, 3H), 3.21 (d, J=18.5 Hz, 1H), 3.16-3.07 (m, 2H), 2.63 (sept, J=6.3 Hz, 1H), 2.23 (s, 3H), 1.17 (d, J=6.6 Hz, 3H), 1.12 (d, J=6.6 Hz, 3H).

$^{13}$C NMR δ (75 MHz, CDCl$_3$) (ppm): 142.4, 135.3, 134.8, 130.3, 130.25, 130.1, 130.0, 129.0, 128.4, 124.6, 123.8, 120.6, 84.1, 72.0, 61.2, 46.6, 32.0, 25.0, 23.7, 23.3, 14.2.

IR (neat) (cm$^{-1}$): $\lambda_{max}$=3462, 3011, 2966, 2931, 2875, 1613, 1479, 1458, 1426, 1393, 1277, 1233, 1158, 1080, 1044, 971, 919, 908, 789, 717, 679, 640.

HRMS (ESI positive):

Calculated for C$_{21}$H$_{26}$N [M-I]$^+$ 292.2065; Found 292.2060.

$[\alpha]_D^{20}$+178° (c 0.54, MeOH).

Compound No 5

Compound No 5 is prepared according to the general procedure D.

To a solution of 70 mg of (5S,10R)-12-(cyclopropylmethyl)-5-methyl-10,11-dihydro-5H-5,10-epiminodibenzo[a,d][7]annulene (0.25 mmol) in 1 mL of dioxane were added 1.25 mL of methyl iodide (20 mmol) to give 113 mg of Compound No 5 as a white solid without purification.

Yield=90%.

Melting point=103-105° C.

$^1$H NMR δ (300 MHz, CDCl$_3$) (ppm): 7.62 (br d, J=6.7 Hz, 1H), 7.37-7.31 (m, 1H), 7.31-7.21 (m, 4H), 7.10-7.03 (m, 2H), 6.12 (d, J=5.1 Hz, 1H), 3.84-3.70 (m, 2H), 3.37 (s, 3H), 3.23-3.10 (m, 2H), 2.26 (s, 3H), 1.51-1.38 (m, 1H), 0.94-0.83 (m, 1H), 0.80-0.69 (m, 2H), 0.51-0.42 (m, 1H).

$^{13}$C NMR δ (75 MHz, CDCl$_3$) (ppm): 143.1, 135.3, 134.7, 130.4, 130.2, 130.0 (2C), 129.3, 128.4, 124.2, 123.7, 120.6, 82.3, 72.2, 58.4, 46.1, 31.8, 14.6, 7.8, 6.7, 3.9.

IR (neat) (cm$^{-1}$): $\lambda_{max}$=3462, 3077, 3000, 2939, 1613, 1478, 1460, 1426, 1391, 1359, 1275, 1173, 1084, 1059, 1032, 991, 917, 840, 788, 767, 717, 639.

HRMS (ESI positive):

Calculated for C$_{21}$H$_{24}$N [M-I]$^+$ 290.1909; Found 290.1909.

$[\alpha]_D^{20}$+126° (c 0.54, MeOH).

Compound No 6

Compound No 6 is prepared according to the general procedure D.

To a solution of 50 mg of (5S,10R)-12-(cyclopentylmethyl)-5-methyl-10,11-dihydro-5H-5,10-epiminodibenzo[a,d][7]annulene (0.16 mmol) in 1 mL of dioxane were added 0.8 mL of methyl iodide (13 mmol) to give 56 mg of Compound No 6 as a yellow solid after purification over preparative plate (eluent: 90% DCM/10% MeOH).

Yield=74%.

Melting point=125-127° C.

$^1$H NMR δ (300 MHz, CDCl$_3$) (ppm): 7.68 (br d, J=6.8 Hz, 1H), 7.38-7.31 (m, 1H), 7.31-7.21 (m, 4H), 7.12-7.04 (m, 2H), 6.23 (d, J=4.9 Hz, 1H), 3.62 (dd, J=18.9 Hz, 5.4 Hz, 1H), 3.42-3.35 (m, 2H), 3.29 (s, 3H), 3.15 (d, J=18.7 Hz, 1H), 2.79-2.65 (m, 1H), 2.24 (s, 3H), 2.10-1.98 (m, 1H), 1.76-1.50 (m, 5H), 1.43-1.32 (m, 1H), 1.27-1.15 (m, 1H).

$^{13}$C NMR δ (75 MHz, CDCl$_3$) (ppm): 142.8, 135.4, 134.6, 130.3, 130.2, 130.1, 130.0, 129.1, 128.4, 124.5, 123.7, 120.6, 83.3, 71.9, 59.5, 46.9, 35.8, 33.8, 33.6, 31.8, 25.3, 24.9, 14.1.

IR (neat) (cm$^{-1}$): $\lambda_{max}$=3462, 3075, 3010, 2960, 2945, 2906, 2869, 1612, 1478, 1459, 1426, 1395, 1359, 1275, 1175, 1081, 1059, 918, 787, 726, 639.

HRMS (ESI positive):

Calculated for C$_{23}$H$_{28}$N [M-I]$^+$ 318.2222; Found 318.2220.

$[\alpha]_D^{20}$+125° (c 0.51, MeOH).

Compound No 7

Compound No 7 is prepared according to the general procedure D.

To a solution of 85 mg of 2-((5S,10R)-5-methyl-10,11-dihydro-5H-5,10-epiminodibenzo[a,d][7]annulen-12-yl) acetimidic acid (0.31 mmol) in 1.5 mL of dioxane was added 1.5 mL of methyl iodide (24.1 mmol) to give 90 mg of Compound No 7 as a white solid without purification.

Yield: 69%.

Melting point=189-192° C.

$^1$H NMR δ (300 MHz, CDCl$_3$) (ppm): 8.49 (br s, 1H), 7.49-7.28 (m, 6H), 7.20-7.14 (m, 1H), 7.13-7.06 (m, 1H), 6.35 (br s, 1H), 5.79 (d, J=5.0 Hz, 1H), 5.48 (d, J=14.5 Hz, 1H), 3.97 (dd, J=18.7 Hz, 5.0 Hz, 1H), 3.8 (d, J=14.5 Hz, 1H), 3.29 (s, 3H), 3.13 (d, J=18.7 Hz, 1H), 2.46 (s, 3H).

$^{13}$C NMR δ (75 MHz, CDCl$_3$) (ppm): 166.0, 141.9, 134.7, 134.1, 130.6, 130.4 (2C), 130.3, 129.1, 128.7, 124.3, 123.6, 121.0, 84.8, 73.6, 54.8, 45.9, 31.8, 14.6.

IR (neat) (cm$^{-1}$): $\lambda_{max}$=3314, 3146, 3013, 1689, 1606, 1477, 1458, 1428, 1413, 1392, 1321, 1273, 1233, 1184, 1114, 1083, 1019, 983, 897, 776, 731.

HRMS (ESI positive):

Calculated for C$_{19}$H$_{21}$N$_2$O [M-I]$^+$ 293.1654; Found 293.1662.

$[\alpha]_D^{20}$+90° (c 0.52, MeOH).

Compound No 8

Compound No 8 is prepared according to the general procedure D.

To a solution of 165 mg of (5S,10R)-12-(4-fluorobenzyl)-5-methyl-10,11-dihydro-5H-5,10-epiminodibenzo[a,d][7] annulene (0.5 mmol) in 2 mL of dioxane was added 2.5 mL of methyl iodide (40.2 mmol) to give 108 mg of Compound No 8 as a yellow solid after purification over preparative plate (eluent: 90% DCM/10% MeOH).

Yield: 46%.

Melting point=92-94° C.

$^1$H NMR δ (300 MHz, CDCl$_3$) (ppm): 7.61-7.51 (m, 3H), 7.50-7.31 (m, 5H), 7.31-7.23 (m, 1H), 7.15-7.05 (m, 3H), 6.24 (d, J=5.6 Hz, 1H), 5.64 (d, J=13.4 Hz, 1H), 4.74 (d, J=13.4 Hz, 1H), 4.13 (dd, J=18.8 Hz, 5.7 Hz, 1H), 3.34 (s, 3H), 3.26 (d, J=18.8 Hz, 1H), 2.00 (s, 3H).

$^{13}$C NMR δ (75 MHz, CDCl$_3$) (ppm): 165.7, 162.4, 143.3, 135.5, 135.4, 135.0, 134.4, 130.9, 130.7, 130.2, 130.1, 129.6, 128.7, 124.2, 123.6, 120.7, 116.8, 116.5, 82.4, 73.6, 57.3, 44.2, 32.3, 15.2.

IR (neat) (cm$^{-1}$): $\lambda_{max}$=3452, 3033, 2934, 1605, 1512, 1478, 1458, 1424, 1392, 1302, 1230, 1163, 1082, 1016, 919, 907, 862, 833, 763, 717, 641.

HRMS (ESI positive):

Calculated for C$_{24}$H$_{23}$NF [M-I]$^+$ 344.1815; Found 344.1812.

$[\alpha]_D^{20}$+153° (c 0.49, MeOH).

Compound No 9

Compound No 9 is prepared according to the general procedure D.

To a solution of 190 mg of (5S,10R)-5-methyl-12-(3-(trifluoromethyl)benzyl)-10,11-dihydro-5H-5,10-epiminodibenzo[a,d][7]annulene (0.5 mmol) in 2 mL of dioxane was added 2.5 mL of methyl iodide (40.2 mmol) to give 75 mg of Compound No 9 as a pale yellow solid after purification over preparative plate (eluent: 90% DCM/10% MeOH).

Yield: 29%.

Melting point=167-170° C.

$^1$H NMR δ (300 MHz, CDCl$_3$) (ppm): 8.04 (d, J=7.9 Hz, 1H), 7.75-7.68 (m, 1H), 7.65-7.55 (m, 2H), 7.49-7.23 (m, 7H), 7.06 (d, J=7.4 Hz, 1H), 6.31 (d, J=5.5 Hz, 1H), 5.81 (d, J=13.2 Hz, 1H), 4.8 (d, J=13.2 Hz, 1H), 4.14 (dd, J=19.0 Hz, 5.5 Hz, 1H), 3.37 (s, 3H), 3.26 (d, J=19.0 Hz, 1H), 1.91 (s, 3H).

$^{13}$C NMR δ (75 MHz, CDCl$_3$) (ppm): 143.1, 137.2, 134.9, 134.3, 131.0, 130.9, 130.5, 130.4, 130.2 (2C), 129.7, 129.4, 128.8 (2C), 127.7, 123.6, 123.5, 120.7 (2C), 82.6, 74.1, 57.7, 44.1, 32.2, 153.

IR (neat) (cm$^{-1}$): λ$_{max}$=3447, 3015, 2928, 1616, 1478, 1453, 1423, 1393, 1329, 1274, 1209, 1182, 1168, 1125, 1018, 971, 919, 871, 808, 728, 642.

HRMS (ESI positive):

Calculated for C$_{25}$H$_{23}$NF$_3$ [M-I]$^+$ 394.1783; Found 394.1779.

[α]$_D^{20}$+136° (c 0.50, MeOH).

Compound No 10

Compound No 10 is prepared according to the general procedure D.

To a solution of 90 mg of (5S,10R)-12-isopentyl-5-methyl-10,11-dihydro-5H-5,10-epiminodibenzo[a,d][7]annulene (0.31 mmol) in 1 mL of dioxane were added 1.5 mL of methyl iodide (24.1 mmol) to give 100 mg of Compound No 10 as a yellow solid without purification.

Yield=74%.

Melting point=215-217° C.

$^1$H NMR δ (300 MHz, CDCl$_3$) (ppm): 7.67 (br d, J=6.9 Hz, 1H), 7.41-7.35 (m, 1H), 7.35-7.25 (m, 4H), 7.13-7.05 (m, 2H), 6.06 (d, J=5.0 Hz, 1H), 3.67-3.44 (m, 3H), 3.29 (s, 3H), 3.16 (d, J=18.9 Hz, 1H), 2.26 (s, 3H), 2.06-1.90 (m, 2H), 1.62 (sept, J=6.6 Hz, 1H), 0.9 (d, J=6.6 Hz, 3H), 0.87 (d, J=6.6 Hz, 3H).

$^{13}$C NMR δ (75 MHz, CDCl$_3$) (ppm): 143.0, 135.2, 134.4, 130.3, 130.2, 130.1, 130.0, 129.2, 128.4, 124.5, 123.8, 120.7, 83.0, 71.5, 53.1, 46.5, 32.4, 31.7, 26.7, 22.8, 22.3, 14.2.

IR (neat) (cm$^{-1}$): λ$_{max}$=3467, 3010, 2958, 2872, 1613, 1481, 1462, 1425, 1393, 1273, 1234, 1160, 1084, 1045, 919, 785, 765, 729, 639.

HRMS (ESI positive):

Calculated for C$_{22}$H$_{28}$N [M-I]$^+$ 306.2222; Found 306.2220.

[α]$_D^{20}$+137° (c 0.54, MeOH).

Compound No 11

Compound No 11 is prepared according to the general procedure D.

To a solution of 66 mg of (5S,10R)-5-methyl-12-propyl-10,11-dihydro-5H-5,10-epiminodibenzo[a,d][7]annulene (0.25 mmol) in 1.25 mL of dioxane was added 1.25 mL of methyl iodide (20.1 mmol) to give 44 mg of Compound No 11 as a yellow solid after purification over preparative plate (eluent: 90% DCM/10% MeOH).

Yield: 42%.

Melting point=214-217° C.

$^1$H NMR δ (300 MHz, CDCl$_3$) (ppm): 7.69 (br d, J=6.4 Hz, 1H), 7.42-7.27 (m, 5H), 7.16-7.07 (m, 2H), 6.12 (d, J=4.7 Hz, 1H), 3.69-3.51 (m, 2H), 3.34 (s, 3H), 3.25-3.10 (m, 2H), 2.27 (s, 3H), 2.23-2.07 (m, 2H), 0.99 (t, J=7.4 Hz, 3H).

$^{13}$C NMR δ (75 MHz, CDCl$_3$) (ppm): 143.1, 135.3, 134.5, 130.4, 130.2, 130.1, 130.0, 129.2, 128.4, 124.5, 123.8, 120.6, 82.9, 71.6, 55.7, 46.6, 31.7, 18.2, 14.0, 11.6.

IR (neat) (cm$^{-1}$): λ$_{max}$=3462, 3008, 2968, 2877, 1612, 1480, 1459, 1425, 1395, 1275, 1261, 1233, 1104, 1081, 1041, 1018, 947, 880, 841, 782, 766, 731, 697.

HRMS (ESI positive):

Calculated for C$_{20}$H$_{24}$N [M-I]$^+$ 278.1909; Found 278.1908.

[α]$_D^{14}$+124° (c 0.17, MeOH).

Compound No 12

Compound No 12 is prepared according to the general procedure D.

To a solution of 82 mg of (5S,10R)-12-hexyl-5-methyl-10,11-dihydro-5H-5,10-epiminodibenzo[a,d][7]annulene (0.26 mmol) in 1.5 mL of dioxane was added 1.3 mL of methyl iodide (21 mmol) to give 43 mg of Compound No 12 as a yellow solid after purification over preparative plate (eluent: 90% DCM/10% MeOH).

Yield=36%.

Melting point=200-203° C.

$^1$H NMR δ (300 MHz, CDCl$_3$) (ppm): 7.69 (m, 1H), 7.42-7.27 (m, 5H), 7.15-7.09 (m, 2H), 6.13 (d, J=5.0 Hz, 1H), 3.63 (dd, J=19.2 Hz, 5.0 Hz, 1H), 3.57-3.48 (m, 1H), 3.35 (s, 3H), 3.33-3.26 (m, 1H), 3.18 (d, J=19.2 Hz, 1H), 2.27 (s, 3H), 2.16-2.03 (m, 2H), 1.46-1.19 (m, 6H), 0.83 (t, J=6.3 Hz, 3H).

$^{13}$C NMR δ (75 MHz, CDCl$_3$) (ppm): 143.0, 135.3, 134.5, 130.31, 130.25, 130.1, 130.0, 129.2, 128.5, 124.5, 123.8, 120.6, 82.9, 71.6, 54.4, 46.5, 31.7, 31.3, 26.8, 24.4, 22.6, 14.1, 13.8.

IR (neat) (cm$^{-1}$): λ$_{max}$=3462, 3075, 3010, 2956, 2927, 2871, 2856, 1614, 1480, 1460, 1425, 1395, 1308, 1275, 1233, 1159, 1082, 920, 809, 783, 748, 639.

HRMS (ESI positive):

Calculated for C$_{23}$H$_{30}$N [M-I]$^+$ 320.2378; Found 320.2378.

[α]$_D^{14}$+150° (c 0.26, MeOH

Compound No 13

Compound No 13 is prepared according to the general procedure D.

To a solution of 100 mg of (5S,10R)-5-methyl-12-(2-methylbutyl)-10,11-dihydro-5H-5,10-epiminodibenzo[a,d][7]annulene (0.34 mmol) in 1.5 mL of dioxane were added 1.5 mL of methyl iodide (24.1 mmol) to give 46 mg of Compound No 13 as a white solid after purification over preparative plate (eluent: 90% DCM/10% MeOH).

Yield=31%.

Melting point=181-184° C.

$^1$H NMR δ (300 MHz, CDCl$_3$) (ppm): 7.74 (br t, J=7.0 Hz, 1H), 7.44-7.29 (m, 5H), 7.15-7.09 (m, 2H), 6.36 (d, J=5.3 Hz, 1H, dia 1), 6.31 (d, J=5.3 Hz, 1H, dia 2), 3.72 (dd, J=18.8 Hz, 5.3 Hz, 1H, dia 1), 3.67 (dd, J=18.8 Hz, 5.3 Hz, 1H, dia 2), 3.41-3.37 (m, 1H), 3.35 (s, 3H, dia 1), 3.33 (s, 3H, dia 2), 3.32-3.15 (m, 3H), 2.53-2.35 (m, 1H), 2.29 (s, 3H, dia 1), 2.28 (s, 3H, dia 2), 1.66-1.53 (m, 1H), 1.27 (d, J=6.5 Hz, 3H, dia 1), 1.21 (d, J=6.5 Hz, 3H, dia 2), 0.97-0.87 (m, 3H).

$^{13}$C NMR δ (75 MHz, CDCl$_3$) (ppm): 142.5 (dia 1), 142.3 (dia 2), 135.4 (dia 1), 135.3 (dia 2), 134.9 (dia 1), 134.8 (dia 2), 130.3, 130.1, 130.0, 129.1 (dia 1) 129.0 (dia 2), 128.5, 124.5, 123.8, 120.7, 120.6, 84.0 (dia 1), 83.9 (dia 2), 72.3

(dia 1), 72.1 (dia 2), 61.1 (dia 1), 60.1 (dia 2), 47.0 (dia 1), 46.1 (dia 2), 32.0 (dia 1), 31.9 (dia 2), 30.8 (dia 1), 30.7 (dia 2), 30.3 (dia 1), 29.6 (dia 2), 20.7 (dia 1), 19.7 (dia 2), 14.2, 11.4 (dia 1), 11.2 (dia 2).

IR (neat) (cm$^{-1}$): $\lambda_{max}$=3452, 3011, 2964, 2933, 2876, 1614, 1479, 1460, 1425, 1395, 1341, 1307, 1274, 1250, 1233, 1191, 1158, 1081, 1045, 1018, 970, 940, 918, 871, 788, 765, 728, 717, 677, 639.

HRMS (ESI positive):
Calculated for $C_{22}H_{28}N$ [M-I]$^+$ 306.2222; Found 306.2219.

$[\alpha]_D^{20}$+180° (c 0.44, MeOH).

Compound No 14

Compound No 14 is prepared according to the general procedure D.

To a solution of 84 mg of (+)-MK801 maleate (0.25 mmol) in 1 mL of dioxane were added 324 mg of cesium carbonate (1 mmol) and 1.6 mL of ethyl iodide (20 mmol) to give 80 mg of Compound No 14 as a white solid without purification.

Yield: 79%.

Melting point=237-238° C.

$^1$H NMR δ (300 MHz, CDCl$_3$) (ppm): 7.63 (d, J=6.8 Hz, 1H), 7.41-7.35 (m, 1H), 7.33-7.21 (m, 4H), 7.12-7.04 (m, 2H), 6.07 (d, J=5.3 Hz, 1H), 3.9 (dd, J=19.5 Hz, 5.4 Hz, 1H), 3.86-3.72 (m, 2H), 3.68-3.53 (m, 1H), 3.38-3.24 (m, 1H), 3.14 (d, 19.5 Hz, 1H), 2.26 (s, 3H), 1.65 (td, J=7.2 Hz, 2.2 Hz, 6H).

$^{13}$C NMR δ (75 MHz, CDCl$_3$) (ppm): 143.7, 135.5, 134.3, 130.4, 130.3, 130.1, 130.0, 129.9, 128.2, 123.7, 123.6, 120.4, 83.8, 68.7, 52.1, 48.0, 32.0, 15.5, 11.5, 11.2.

IR (neat) (cm$^{-1}$): $\lambda_{max}$=3467, 3019, 2981, 2829, 1613, 1484, 1460, 1452, 1428, 1396, 1308, 1295, 1250, 1231, 1153, 1133, 1076, 1040, 918, 903, 804, 787, 717, 641.

HRMS (ESI positive):
Calculated for $C_{20}H_{24}N$ [M-I]$^+$ 278.1909; Found 278.1919.

$[\alpha]_D^{20}$+200° (c 0.50, MeOH).

Compound No 15

Compound No 15 is prepared according to the general procedure D.

To a solution of 100 mg of (5S,10R)-12-(cyclohexylmethyl)-5-methyl-10,11-dihydro-5H-5,10-epiminodibenzo[a,d][7]annulene (0.32 mmol) in 1.5 mL of dioxane was added 1.5 mL of methyl iodide (24.1 mmol) to give 33 mg of Compound No 15 as a yellow solid after purification over preparative plate (eluent: 90% DCM/10% MeOH).

Yield=18%.

Melting point=220-222° C.

$^1$H NMR δ (300 MHz, CDCl$_3$) (ppm): 7.70 (d, J=7.0 Hz, 1H), 7.42-7.27 (m, 5H), 7.15-7.07 (m, 2H), 6.33 (d, J=5.0 Hz, 1H), 3.67 (dd, J=19.1 Hz, 5.0 Hz, 1H), 3.35 (s, 3H), 3.24-3.12 (m, 3H), 2.44-2.33 (m, 1H), 2.26 (s, 3H), 2.05-1.92 (m, 2H), 1.80-1.41 (m, 4H), 1.30-0.97 (m, 4H).

$^{13}$C NMR δ (75 MHz, CDCl$_3$) (ppm): 142.5, 135.4, 134.9, 130.4, 130.3, 130.2, 130.0, 129.2, 128.5, 124.5, 123.8, 120.7, 83.8, 72.3, 60.9, 46.8, 34.0, 33.8, 33.5, 32.0, 26.0, 25.8, 25.0, 14.2.

IR (neat) (cm$^{-1}$): $\lambda_{max}$=3437, 3009, 2953, 1613, 1478, 1461, 1448, 1425, 1396, 1357, 1275, 1183, 1018, 919, 788, 765, 728, 639.

HRMS (ESI positive):
Calculated for $C_{24}H_{30}N$ [M-I]$^+$ 332.2378; Found 332.2385.

$[\alpha]_D^{20}$+126° (c 0.27, MeOH).

Compound No 16

Compound No 16 is prepared according to the general procedure D.

To a solution of 60 mg of (5S,10R)-12-benzyl-5-methyl-10,11-dihydro-5H-5,10-epiminodibenzo[a,d][7]annulene (0.19 mmol) in 1 mL of dioxane was added 0.8 mL of methyl iodide (13 mmol) to give 24 mg of Compound No 16 as a white solid after purification over preparative plate (eluent: 90% DCM/10% MeOH).

Yield: 28%.

Melting point=220-222° C.

$^1$H NMR δ (300 MHz, CDCl$_3$) (ppm): 7.57 (d, J=7.2 Hz, 1H), 7.50-7.29 (m, 10H), 7.29-7.22 (m, 1H), 7.05 (d, J=7.4 Hz, 1H), 6.28 (d, J=5.5 Hz, 1H), 5.61 (d, J=13.2 Hz, 1H), 4.71 (d, J=13.2 Hz, 1H), 4.14 (dd, J=18.8 Hz, 5.9 Hz, 1H), 3.33 (s, 3H), 3.23 (d, J=18.8 Hz, 1H), 1.96 (s, 3H).

$^{13}$C NMR δ (75 MHz, CDCl$_3$) (ppm): 143.5, 135.2, 134.6, 133.4 (2C), 130.9 (2C), 130.6, 130.2, 130.1, 129.8, 129.4 (2C), 128.6, 128.3, 123.7, 123.6, 120.6, 82.2, 73.8, 58.5, 44.1, 32.2, 15.1.

IR (neat) (cm$^{-1}$): $\lambda_{max}$=3457, 3067, 3008, 2959, 2921, 2851, 1605, 1584, 1498, 1458, 1422, 1393, 1303, 1273, 1250, 1180, 1134, 1078, 1049, 1033, 970, 919, 907, 761, 732, 704, 639.

HRMS (ESI positive):
Calculated for $C_{24}H_{24}N$ [M-I]$^+$ 326.1909; Found 326.1908. $[^{13}]_D^{15}$+93° (c 0.05, MeOH).

Compound No 17

Compound No 17 is prepared according to the general procedure D.

To a solution of 80 mg of (5S,10R)-12-(cyclobutylmethyl)-5-methyl-10,11-dihydro-5H-5,10-epiminodibenzo[a,d][7]annulene (0.28 mmol) in 1.5 mL of dioxane were added 1.4 mL of methyl iodide (22.5 mmol) to give 31 mg of Compound No 17 as a yellow solid after purification over preparative plate (eluent: 90% DCM/10% MeOH).

Yield=25%.

Melting point=159-162° C.

$^1$H NMR δ (300 MHz, CDCl$_3$) (ppm): 7.7 (br d, J=6.9 Hz, 1H), 7.40-7.27 (m, 5H), 7.15-7.05 (m, 2H), 6.36 (d, J=5.2 Hz, 1H), 3.64 (dd, J=18.6 Hz, 5.2 Hz, 1H), 3.48-3.41 (m, 2H), 3.22 (s, 3H), 3.16 (d, J=18.6 Hz, 1H), 2.51-2.41 (m, 1H), 2.25 (s, 3H), 2.11-2.00 (m, 2H), 1.91-1.77 (m, 2H).

$^{13}$C NMR δ (75 MHz, CDCl$_3$) (ppm): 142.8, 135.3, 134.5, 130.4, 130.2, 130.1, 130.0, 129.2, 128.4, 124.5, 123.7, 120.6, 82.6, 71.8, 58.9, 46.2, 31.7, 31.0, 30.6, 27.3, 18.8, 14.1.

IR (neat) (cm$^{-1}$): $\lambda_{max}$=3430, 3075, 2960, 2933, 2906, 1613, 1478, 1459, 1426, 1394, 1341, 1256, 1234, 1159, 1076, 1058, 1041, 1017, 971, 918, 909, 840, 764, 727, 639.

HRMS (ESI positive):
Calculated for $C_{22}H_{26}N$ [M-I]$^+$ 304.2041; Found 304.045. $[\alpha]_D^{20}$+121° (c 0.29, MeOH).

Compound No 18

Compound No 18 is prepared according to the general procedure D.

To a solution of 140 mg of (5S,10R)-5-methyl-12-((1-phenylcyclopropyl)methyl)-10,11-dihydro-5H-5,10-epiminodibenzo[a,d][7]annulene (0.36 mmol) in 2 mL of dioxane were added 1.8 mL of methyl iodide (28.9 mmol) to give 80 mg of Compound No 18 as a yellow solid after purification over preparative plate (eluent: 90% DCM/10% MeOH).

Yield: 45%.

Melting point=174-176° C.

$^1$H NMR δ (300 MHz, CDCl$_3$) (ppm): 7.48-7.26 (m, 9H), 7.25-7.20 (m, 2H), 7.04-6.93 (m, 2H), 4.99 (d, J=5.4 Hz, 1H), 4.25 (d, J=14.2 Hz, 1H), 3.58 (d, J=14.2 Hz, 1H), 3.31 (s, 3H), 3.24 (dd, J=18.9 Hz, 5.4 Hz, 1H), 2.65 (d, J=18.9

Hz, 1H), 2.10 (s, 3H), 1.71-1.61 (m, 1H), 1.43-1.33 (m, 1H), 1.32-1.22 (m, 1H), 0.96-0.86 (m, 1H).

$^{13}$C NMR δ (75 MHz, CDCl$_3$) (ppm): 142.1, 141.9, 134.8, 134.7, 130.3, 130.2 (2C), 130.1 (2C), 130.0, 129.6 (2C), 129.0, 128.6, 128.4, 124.1, 123.3, 121.0, 83.9, 73.0, 62.7, 45.9, 31.6, 23.1, 15.5, 15.0, 14.9.

IR (neat) (cm$^{-1}$): λ$_{max}$=3450, 3005, 2959, 2921, 1605, 1495, 1478, 1460, 1444, 1424, 1395, 1306, 1277, 1232, 1183, 1115, 1073, 1039, 990, 919, 905, 836, 764, 725, 703, 675, 640.

HRMS (ESI positive):
Calculated for C$_{27}$H$_{28}$N [M-I]$^+$ 366.2222; Found 366.2216.

[α]$_D^{15}$+116° (c 0.50, MeOH).

Compound No 19

Compound No 19 is prepared according to the general procedure D.

To a solution of 163 mg of (5S,10R)-5-methyl-12-(4-methylbenzyl)-10,11-dihydro-5H-5,10-epiminodibenzo[a,d][7]annulene (0.5 mmol) in 2 mL of dioxane was added 2.5 mL of methyl iodide (40.2 mmol) to give 97 mg of Compound No 19 as a pale yellow solid after purification over preparative plate (eluent: 90% DCM/10% MeOH).

Yield: 42%.

Melting point=134-136° C.

$^1$H NMR δ (300 MHz, CDCl$_3$) (ppm): 7.55 (d, J=7.0 Hz, 1H), 7.47-7.27 (m, 7H), 7.24-7.13 (m, 3H), 7.05 (d, J=7.3 Hz, 1H), 6.15 (d, J=5.2 Hz, 1H), 5.39 (d, J=13.3 Hz, 1H), 4.64 (d, J=13.3 Hz, 1H), 4.11 (dd, J=19.1 Hz, 5.8 Hz, 1H), 3.26 (s, 3H), 3.23 (d, J=19.1 Hz, 1H), 2.32 (s, 3H), 1.97 (s, 3H).

$^{13}$C NMR δ (75 MHz, CDCl$_3$) (ppm): 143.5, 141.1, 135.2, 134.6, 133.1 (2C), 130.8, 130.5, 130.11, 130.07 (2C), 130.0, 129.7, 128.5, 125.1, 123.6 (2C), 120.6, 82.1, 73.6, 58.3, 44.2, 32.3, 21.5, 15.1.

IR (neat) (cm$^{-1}$): λ$_{max}$=3457, 3052, 3013, 2952, 2920, 1737, 1613, 1478, 1457, 1422, 1393, 1326, 1272, 1206, 1176, 1083, 1051, 920, 907, 887, 808, 787, 730, 638.

HRMS (ESI positive):
Calculated for C$_{25}$H$_{26}$N [M-I]$^+$ 340.2065; Found 340.2072.

[α]$_D^{20}$+124° (c 0.56, MeOH).

Compound No 20

Compound No 20 is prepared according to the general procedure D.

To a solution of 184 mg of (5S,10R)-12-(4-(tert-butyl)benzyl)-5-methyl-10,11-dihydro-5H-5,10-epiminodibenzo[a,d][7]annulene (0.5 mmol) in 2 mL of dioxane was added 2.5 mL of methyl iodide (40.2 mmol) to give 83 mg of Compound No 20 as a pale yellow solid after purification over preparative plate (eluent: 90% DCM/10% MeOH).

Yield: 33%.

Melting point=152-154° C.

$^1$H NMR δ (300 MHz, CDCl$_3$) (ppm): 7.56 (d, J=7.0 Hz, 1H), 7.49-7.35 (m, 7H), 7.35-7.27 (m, 2H), 7.25-7.19 (m, 1H), 7.07 (d, J=7.0 Hz, 1H), 6.11 (d, J=5.5 Hz, 1H), 5.39 (d, J=13.3 Hz, 1H), 4.67 (d, J=13.3 Hz, 1H), 4.12 (dd, J=18.9 Hz, 5.5 Hz, 1H), 3.29 (s, 3H), 3.24 (d, J=18.9 Hz, 1H), 2.01 (s, 3H), 1.27 (s, 9H).

$^{13}$C NMR δ (75 MHz, CDCl$_3$) (ppm): 154.2, 143.5, 135.2, 134.5, 132.9 (2C), 130.7, 130.5, 130.1, 130.0, 129.7, 128.5, 126.4 (2C), 125.1, 123.7, 123.6, 120.7, 82.2, 73.5, 58.1, 44.4, 35.0, 32.3, 31.3 (3C), 15.2.

IR (neat) (cm$^{-1}$): λ$_{max}$=3452, 3014, 2965, 2905, 2868, 1813, 1613, 1515, 1477, 1459, 1422, 1393, 1365, 1337, 1303, 1269, 1233, 1179, 1160, 1133, 1111, 1082, 1051, 1018, 970, 919, 907, 888, 860, 840, 820, 790, 772, 730, 718, 674, 639.

HRMS (ESI positive):
Calculated for C$_{28}$H$_{32}$N [M-I]$^+$ 382.2535; Found 382.2542.

[α]$_D^{20}$+115° (c 0.55, MeOH).

Compound No 21

Compound No 21 is prepared according to the general procedure D.

To a solution of 200 mg of (5S,10R)-12-(4-methoxybenzyl)-5-methyl-10,11-dihydro-5H-5,10-epiminodibenzo[a,d][7]annulene (0.6 mmol) in 2 mL of dioxane was added 2.5 mL of methyl iodide (40.2 mmol) to give 95 mg of Compound No 21 as a pale yellow solid after purification over preparative plate (eluent: 90% DCM/10% MeOH).

Yield: 39%.

Melting point=101-103° C.

$^1$H NMR δ (300 MHz, CDCl$_3$) (ppm): 7.55 (d, J=7.0 Hz, 1H), 7.47-7.35 (m, 5H), 7.35-7.27 (m, 2H), 7.24-7.19 (m, 1H), 7.05 (d, J=7.3 Hz, 1H), 6.88 (d, J=8.7 Hz, 2H), 6.12 (d, J=5.4 Hz, 1H), 5.4 (d, J=13.5 Hz, 1H), 4.64 (d, J=13.5 Hz, 1H), 4.1 (dd, J=18.9 Hz, 5.4 Hz, 1H), 3.79 (s, 3H), 3.26 (s, 3H), 3.22 (d, J=18.9 Hz, 1H), 1.98 (s, 3H).

$^{13}$C NMR δ (75 MHz, CDCl$_3$) (ppm): 161.4, 143.5, 135.2, 134.7 (2C), 130.8, 130.5, 130.1, 130.0, 129.7, 128.5, 123.6 (2C), 120.6, 119.9, 114.7 (2C), 81.9, 73.4, 58.1, 55.6, 44.1, 32.2, 15.1.

IR (neat) (cm$^{-1}$): λ$_{max}$=3447, 3011, 2936, 2888, 1813, 1815, 1610, 1582, 1515, 1478, 1459, 1421, 1392, 1337, 1282, 1257, 1182, 1111, 1083, 1051, 919, 905, 887, 825, 787, 762, 731, 640.

HRMS (ESI positive):
Calculated for C$_{25}$H$_{26}$NO [M-I]$^+$ 356.2014; Found 356.2021.

[α]$_D^{20}$+115° (c 0.52, MeOH).

Compound No 22

Compound No 22 is prepared according to the general procedure D.

To a solution of 173 mg of (5S,10R)-12-(4-chlorobenzyl)-5-methyl-10,11-dihydro-5H-5,10-epiminodibenzo[a,d][7]annulene (0.5 mmol) in 2 mL of dioxane was added 2.5 mL of methyl iodide (40.2 mmol) to give 70 mg of Compound No 22 as a yellow solid after purification over preparative plate (eluent: 90% DCM/10% MeOH).

Yield: 29%.

Melting point=160-162° C.

$^1$H NMR δ (300 MHz, CDCl$_3$) (ppm): 7.56 (d, J=7.1 Hz, 1H), 7.53-7.47 (m, 2H), 7.47-7.27 (m, 7H), 7.26-7.21 (m, 1H), 7.07 (d, J=7.1 Hz, 1H), 6.17 (d, J=5.3 Hz, 1H), 5.54 (d, J=13.3 Hz, 1H), 4.7 (d, J=13.3 Hz, 1H), 4.11 (dd, J=19.2 Hz, 5.3 Hz, 1H), 3.29 (s, 3H), 3.25 (d, J=19.2 Hz, 1H), 2.01 (s, 3H).

$^{13}$C NMR δ (75 MHz, CDCl$_3$) (ppm): 143.2, 137.2, 135.0, 134.7 (2C), 134.4, 130.9, 130.7, 130.3, 130.1, 129.7 (2C), 129.6, 128.7, 126.8, 123.6 (2C), 120.7, 82.5, 73.7, 57.3, 44.2, 32.3, 15.3.

IR (neat) (cm$^{-1}$): λ$_{max}$=3452, 3049, 3019, 2929, 1813, 1596, 1493, 1477, 1455, 1424, 1392, 1338, 1297, 1248, 1181, 1084, 1050, 1015, 970, 919, 907, 837, 814, 789, 723, 691, 671, 640.

HRMS (ESI positive):
Calculated for C$_{24}$H$_{23}$NCl [M-I]$^+$ 360.1519; Found 360.1516.

[α]$_D^{20}$+115° (c 0.50, MeOH).

Compound No 23

Compound No 23 is prepared according to the general procedure D.

To a solution of 173 mg of (5S,10R)-12-(2-chlorobenzyl)-5-methyl-10,11-dihydro-5H-5,10-epiminodibenzo[a,d][7]annulene (0.5 mmol) in 2 mL of dioxane was added 2.5 mL of methyl iodide (40.2 mmol) to give 11 mg of Compound No 23 as a yellow solid after purification over preparative plate (eluent: 90% DCM/10% MeOH).

Yield: 5%.

Melting point=129-131° C.

$^1$H NMR δ (300 MHz, CDCl$_3$) (ppm): 8.10 (d, J=7.7 Hz, 1H), 7.7 (d, J=7.7 Hz, 1H), 7.51-7.44 (m, 1H), 7.43-7.18 (m, 8H), 7.18-7.13 (m, 1H), 6.55 (d, J=5.5 Hz, 1H), 5.13 (d, J=13.8 Hz, 1H), 4.73 (d, J=13.8 Hz, 1H), 4.16 (dd, J=19.3 Hz, 5.5 Hz, 1H), 3.34 (d, J=19.3 Hz, 1H), 3.00 (s, 3H), 3.25 (d, J=19.2 Hz, 1H), 2.07 (s, 3H).

$^{13}$C NMR δ (75 MHz, CDCl$_3$) (ppm): 142.6, 135.8, 135.2, 134.6, 134.4, 132.3, 130.7, 130.6, 130.4, 130.1, 129.9, 129.3, 129.0, 128.2, 126.2, 124.3, 124.0, 120.2, 83.1, 73.8, 53.9, 43.9, 32.5, 13.6.

IR (neat) (cm$^{-1}$): λ$_{max}$=3452, 3038, 2929, 1593, 1477, 1457, 1421, 1391, 1271, 1233, 1206, 1161, 1134, 1057, 1041, 1018, 970, 918, 763, 715, 682, 639.

HRMS (ESI positive):

Calculated for C$_{24}$H$_{23}$NCl [M-I]$^+$ 360.1519; Found 360.1519.

[α]$_D^{20}$+121° (c 0.55, MeOH).

Compound No 24

Compound No 24 is prepared according to the general procedure D.

To a solution of 163 mg of (5S,10R)-5-methyl-12-(2-methylbenzyl)-10,11-dihydro-5H-5,10-epiminodibenzo[a,d][7]annulene (0.5 mmol) in 2.5 mL of dioxane was added 2.5 mL of methyl iodide (40.2 mmol) to give 30 mg of Compound No 24 as a pale yellow solid after purification over preparative plate (eluent: 90% DCM/10% MeOH).

Yield: 14%.

Melting point=101-103° C.

$^1$H NMR δ (300 MHz, CDCl$_3$) (ppm): 7.61 (d, J=7.1 Hz, 1H), 7.47-7.14 (m, 10H), 7.02 (d, J=7.1 Hz, 1H), 6.66 (d, J=5.4 Hz, 1H), 5.51 (d, J=13.9 Hz, 1H), 4.64 (d, J=13.9 Hz, 1H), 4.19 (dd, J=19.5 Hz, 5.4 Hz, 1H), 3.22 (d, J=19.5 Hz, 1H), 3.12 (s, 3H), 2.34 (s, 3H), 1.91 (s, 3H).

$^{13}$C NMR δ (75 MHz, CDCl$_3$) (ppm): 143.4, 140.1, 135.2, 134.6, 134.0, 132.2, 131.0 (2C), 130.6, 130.2, 130.0, 129.8, 128.5, 127.0, 126.9, 124.0, 123.7, 120.4, 82.4, 74.5, 56.4, 43.9, 32.4, 21.3, 14.6.

IR (neat) (cm$^{-1}$): λ$_{max}$=3442, 3023, 2924, 1605, 1493, 1459, 1420, 1391, 1272, 1255, 1232, 1161, 1082, 1047, 1018, 906, 882, 785, 768, 751, 717, 640.

HRMS (ESI positive):

Calculated for C$_{25}$H$_{26}$N [M-I]$^+$ 340.2065; Found 340.2059.

[α]$_D^{20}$+92° (c 0.49, MeOH).

Compound No 25

Compound No 25 is prepared according to the general procedure D.

To a solution of 115 mg of 2-((5S,10R)-5-methyl-10,11-dihydro-5H-5,10-epiminodibenzo[a,d][7]annulen-12-yl)ethan-1-ol (0.43 mmol) in 2 mL of dioxane was added 2 mL of methyl iodide (32.1 mmol) to give 163 mg of Compound No 25 as a pale green solid without purification.

Yield: 93%.

Melting point=216-219° C.

$^1$H NMR δ (300 MHz, CDCl$_3$) (ppm): 7.51 (br d, J=7.2 Hz, 1H), 7.39-7.27 (m, 5H), 7.15-7.08 (m, 2H), 5.89 (d, J=5.2 Hz, 1H), 4.57 (t, J=5.0 Hz, 1H) 4.50-4.37 (m, 1H) 4.17 (dd, J=18.9 Hz, 5.4 Hz, 1H), 4.13-4.03 (m, 1H), 3.66-3.48 (m, 2H), 3.39 (s, 3H), 3.04 (d, J=18.9 Hz, 1H), 2.24 (s, 3H).

$^{13}$C NMR δ (75 MHz, CDCl$_3$) (ppm): 142.1, 135.5, 135.0, 130.7, 130.3, 130.1, 130.0, 129.5, 128.2, 123.8, 123.6, 120.7, 83.6, 73.5, 56.2, 55.0, 46.1, 32.2, 13.7.

IR (neat) (cm$^{-1}$): λ$_{max}$=3313, 2969, 2871, 1610, 1478, 1458, 1393, 1276, 1258, 1231, 1078, 1041, 1018, 957, 883, 763, 727, 720.

HRMS (ESI positive):

Calculated for C$_{19}$H$_{22}$NO [M-I]$^+$ 280.1701; Found 280.1706.

[α]$_D^{14}$+188° (c 0.51, MeOH).

Compound No 26

Compound No 26 is prepared according to the general procedure D.

To a solution of 115 mg of 2-((5S,10R)-5-methyl-10,11-dihydro-5H-5,10-epiminodibenzo[a,d][7]annulen-12-yl)ethan-1-ol (0.4 mmol) in 2 mL of dioxane were added 2.7 mL of ethyl iodide (33.8 mmol) to give 134 mg of Compound No 26 as a pale green solid without purification.

Yield: 80%.

Melting point=202-205° C.

$^1$H NMR δ (300 MHz, CDCl$_3$) (ppm): 7.52 (d, J=6.7 Hz, 1H), 7.40-7.23 (m, 5H), 7.15-7.07 (m, 2H), 5.79 (d, J=5.1 Hz, 1H), 4.50 (br s, 1H), 4.25-3.96 (m, 4H), 369-3.62 (m, 2H), 3.45-3.34 (m, 1H), 3.06 (d, J=19.0 Hz, 1H), 2.31 (s, 3H), 1.44 (t, J=7.1 Hz, 3H).

$^{13}$C NMR δ (75 MHz, CDCl$_3$) (ppm): 143.1, 135.5, 134.9, 130.6, 130.2, 130.1 (2C), 129.6, 128.2, 123.7, 123.2, 120.5, 85.0, 69.0, 56.5, 54.5, 54.3, 32.2, 14.5, 11.9.

IR (neat) (cm$^{-1}$): λ$_{max}$=3314, 3013, 2921, 2820, 1612, 1478, 1461, 1429, 1405, 1393, 1340, 1271, 1228, 1177, 1159, 1089, 1042, 1029, 975, 926, 789, 766, 731, 696, 654, 631.

HRMS (ESI positive):

Calculated for C$_{20}$H$_{24}$NO [M-I]$^+$ 294.1858; Found 294.1853.

[α]$_D^{20}$+155° (c 0.49, MeOH).

Compound No 27

Compound No 27 is prepared according to the general procedure D.

To a solution of 110 mg of 2-(5-methyl-10,11-dihydro-5H-5,10-epiminodibenzo[a,d][7]annulen-12-yl)ethan-1-ol (0.4 mmol) in 2 mL of dioxane were added 2.7 mL of ethyl iodide (33.8 mmol) to give 71 mg of Compound No 27 after purification over preparative plate (eluent: 90% DCM/10% MeOH).

Yield: 42%.

Melting point=205-208° C.

$^1$H NMR δ (300 MHz, CDCl$_3$) (ppm): 7.51 (br d, J=6.7 Hz, 1H), 7.40-7.28 (m, 5H), 7.18-7.07 (m, 2H), 5.82 (d, J=5.1 Hz, 1H), 4.63 (br s, 1H), 4.28-3.93 (m, 4H), 3.74-3.44 (m, 3H), 3.07 (d, J=19.0 Hz, 1H), 2.29 (s, 3H), 1.46 (t, J=7.1 Hz, 3H).

$^{13}$C NMR δ (75 MHz, MeOD) (ppm): 145.0, 137.5, 136.1, 131.3, 131.1 (2C), 131.0, 129.2, 125.3, 124.3, 121.9, 86.5, 71.7, 69.9, 57.6, 55.9, 55.0, 32.6, 13.7, 11.4.

IR (neat) (cm$^{-1}$): λ$_{max}$=3279, 2916, 2886, 1614, 1476, 1455, 1424, 1405, 1380, 1339, 1314, 1271, 1224, 1169, 1090, 1028, 1011, 973, 949, 927, 898, 857, 789, 768, 753, 734, 717, 693, 652, 627.

HRMS (ESI positive):

Calculated for C$_{20}$H$_{24}$NO [M-I]$^+$ 294.1858; Found 294.1854.

[α]$_D^{20}$ 0° (c 0.60, MeOH).

Compound No 28

Compound No 28 is prepared according to the general procedure D.

To a solution of 98 mg of 2-((5S,10R)-5-methyl-10,11-dihydro-5H-5,10-epiminodibenzo[a,d][7]annulen-12-yl)acetonitrile (0.38 mmol) in 2 mL of dioxane was added 2 mL of methyl iodide (32.1 mmol) to give 126 mg of Compound No 28 as a beige solid without purification.

Yield: 82%.

Melting point=147-149° C.

$^1$H NMR δ (300 MHz, CDCl$_3$) (ppm): 7.59 (br d, J=7.0 Hz, 1H), 7.50-7.33 (m, 5H), 7.24-7.14 (m, 2H), 6.45 (d, J=5.2 Hz, 1H), 6.23 (d, J=16.6 Hz, 1H), 4.91 (d, J=16.6 Hz, 1H), 4.0 (dd, J=19.2 Hz, 1H), 3.65 (s, 3H), 3.23 (d, J=19.2 Hz, 1H), 2.44 (s, 3H).

$^{13}$C NMR δ (75 MHz, CDCl$_3$) (ppm): 141.6, 133.8, 133.0, 131.2, 131.0, 130.7, 130.5, 129.0, 128.1, 124.1, 123.9, 120.7, 111.4, 84.9, 74.8, 46.2, 43.7, 31.4, 14.7.

IR (neat) (cm$^{-1}$): $\lambda_{max}$=3450, 2890, 2810, 1611, 1478, 1460, 1394, 1341, 1276, 1255, 1235, 1115, 1083, 1056, 1019, 988, 962, 918, 905, 886, 839, 784, 765, 718, 677, 640.

HRMS (ESI positive):

Calculated for C$_{19}$H$_{19}$N$_2$ [M-I]$^+$ 275.1548; Found 275.1547.

$[α]_D^{20}$+129° (c 0.54, MeOH).

Compound No 29

Compound No 29 is prepared according to the general procedure D.

To a solution of 92 mg of N-(2-((5S,10R)-5-methyl-10,11-dihydro-5H-5,10-epiminodibenzo[a,d][7]annulen-12-yl)ethyl)acetamide (0.3 mmol) in 1.5 mL of dioxane was added 1.5 mL of methyl iodide (24.1 mmol) to give 90 mg of Compound No 29 as a yellow solid after purification over preparative plate (eluent: 90% DCM/10% MeOH).

Yield: 28%.

Melting point=216-218° C.

$^1$H NMR δ (300 MHz, CDCl$_3$) (ppm): 8.03 (t, J=5.2 Hz, 1H), 7.56 (br d, J=6.9 Hz, 1H), 7.40-7.27 (m, 5H), 7.17-7.08 (m, 2H), 5.88 (d, J=4.8 Hz, 1H), 4.03 (dd, J=18.8 Hz, 5.2 Hz, 1H) 3.92 (q, J=5.7 Hz, 2H), 3.83-3.70 (m, 1H), 3.52-3.40 (m, 1H), 3.36 (s, 3H), 3.09 (d, J=18.8 Hz, 1H), 2.21 (s, 3H), 2.03 (s, 3H).

$^{13}$C NMR δ (75 MHz, CDCl$_3$) (ppm): 172.1, 142.3, 134.6, 134.5, 130.8, 130.5, 130.3 (2C), 128.9, 128.4, 124.0, 123.5, 120.8, 84.0, 72.0, 52.4, 46.5, 34.9, 31.7, 23.4, 13.3.

IR (neat) (cm$^{-1}$): $\lambda_{max}$=3250, 3043, 2939, 1666, 1479, 1461, 1442, 1392, 1370, 1276, 1020, 905, 784, 764, 716, 644.

HRMS (ESI positive):

Calculated for C$_{21}$H$_{25}$N$_2$O [M-I]$^+$ 321.1967; Found 321.1964.

$[α]_D^{20}$+130° (c 0.20, MeOH).

Compound No 30

Compound No 30 is prepared according to the general procedure D.

To a solution of 343 mg of (5S,10R)-5-methyl-12-((1-phenylcyclopropyl)methyl)-10,11-dihydro-5H-5,10-epiminodibenzo[a,d][7]annulene (0.89 mmol) in 3 mL of dioxane were added 4.6 mL of methyl iodide (73.9 mmol) to give 260 mg of Compound No 30 as a beige solid after purification over preparative plate (eluent: 90% DCM/10% MeOH).

Yield: 55%.

Melting point=162-164° C.

$^1$H NMR δ (300 MHz, CDCl$_3$) (ppm): 7.53-7.27 (m, 10H), 7.07-6.99 (m, 2H), 5.25 (d, J=5.1 Hz, 1H), 4.38 (d, J=14.2 Hz, 1H), 3.66 (d, J=14.2 Hz, 1H), 3.34 (s, 3H), 3.31 (dd, J=18.9 Hz, 5.0 Hz, 1H), 2.77 (d, J=18.9 Hz, 1H), 2.14 (s, 3H), 1.71-1.61 (m, 1H), 1.51-1.41 (m, 1H), 1.32-1.22 (m, 1H), 1.00-0.90 (m, 1H).

$^{13}$C NMR δ (75 MHz, CDCl$_3$) (ppm): 142.1, 140.7, 134.8, 134.7, 134.2, 131.6 (2C), 130.4, 130.2, 130.11, 130.07, 129.8 (2C), 129.0, 128.5, 124.0, 123.5, 120.9, 83.8, 73.1, 62.5, 45.9, 31.7, 22.6, 15.7, 15.4, 15.1.

IR (neat) (cm$^{-1}$): $\lambda_{max}$=3423, 3013, 2959, 2851, 1605, 1494, 1479, 1459, 1425, 1396, 1306, 1275, 1232, 1183, 1114, 1092, 1039, 1013, 991, 919, 905, 832, 764, 718, 677, 640.

HRMS (ESI positive):

Calculated for C$_{27}$H$_{27}$NCl [M-I]$^+$ 400.1832; Found 400.1826.

$[α]_D^{15}$+102° (c 0.50, MeOH).

Compound No 31

Compound No 31 is prepared according to the general procedure D.

To a solution of 170 mg of (5S,10R)-12-(cyclopropylmethyl)-5-methyl-10,11-dihydro-5H-5,10-epiminodibenzo[a,d][7]annulene (0.62 mmol) in 3 mL of dioxane was added 4 mL of iodoethane (50 mmol) to give 55 mg of Compound No 31 as a white solid after purification over preparative plate (eluent: 95% DCM/5% MeOH).

Yield=21%.

Melting point=189-191° C.

$^1$H NMR δ (300 MHz, CDCl$_3$) (ppm): 7.62 (br d, J=7.0 Hz, 1H), 7.43-7.26 (m, 5H), 7.14-7.07 (m, 2H), 6.06 (d, J=5.3 Hz, 1H), 4.14 (dd, J=14.1 Hz, 4.6 Hz, 1H), 4.07 (dd, J=14.1 Hz, 7.5 Hz, 1H), 3.99 (dd, J=19.4 Hz, 5.4 Hz, 1H), 3.32-3.18 (m, 1H), 3.14 (d, J=19.4 Hz, 1H), 3.12-3.03 (m, 1H), 2.38 (s, 3H), 1.58 (t, J=7.2 Hz, 3H), 1.31-1.20 (m, 1H), 0.86-0.69 (m, 2H), 0.47-0.37 (m, 1H), 0.35-0.26 (m, 1H).

$^{13}$C NMR δ (75 MHz, CDCl$_3$) (ppm): 143.8, 135.5, 134.2, 130.5, 130.3, 130.1, 130.0, 129.9, 128.2, 123.5 (2C), 120.4, 83.2, 68.0, 57.4, 51.8, 31.9, 15.4, 11.0, 7.8, 6.9, 5.5.

IR (neat) (cm$^{-1}$): $\lambda_{max}$=3452, 2998, 2929, 1614, 1461, 1428, 1394, 1340, 1295, 1272, 1250, 1230, 1157, 1113, 1077, 1058, 1030, 919, 840, 788, 764, 718, 639.

HRMS (ESI positive):

Calculated for C$_{22}$H$_{26}$N [M-I]$^+$ 304.2065; Found 304.2059.

$[α]_D^{20}$+113° (c 0.51, MeOH).

Compound No 32

To a solution of 90 mg of Compound No 26 (0.22 mmol) in 5 mL of methanol was added amberlite IRA-400 chloride (440 mg) and the mixture was stirred at room temperature for 2 h. After filtration, the solution was concentrated under vacuum to give 70 mg of Compound No 32 as a pale pink solid without any purification.

Melting point=115-120° C.

$^1$H NMR δ (300 MHz, CDCl$_3$) (ppm): 7.51 (br d, J=7.1 Hz, 1H), 7.40-7.27 (m, 5H), 7.13 (d, J=7.1 Hz, 1H), 7.08 (br d, J=7.1 Hz, 1H), 5.93 (d, J=4.9 Hz, 1H), 4.26 (dd, J=19 Hz, 5.6 Hz, 2H), 4.11-4.01 (m, 1H), 3.99-3.90 (m, 1H), 3.76-3.55 (m, 3H), 3.46-3.38 (m, 1H), 3.05 (d, J=19.0 Hz, 1H), 2.26 (s, 3H), 1.46 (t, J=7.1 Hz, 3H).

$^{13}$C NMR δ (75 MHz, CDCl$_3$) (ppm): 143.1, 135.6, 135.3, 130.6, 130.2, 130.1, 130.0, 128.1, 123.5, 123.3, 120.3, 84.6, 70.8, 69.7, 56.6, 54.6, 54.3, 32.2, 14.2, 11.8.

IR (neat) (cm$^{-1}$): $\lambda_{max}$=3378, 2918, 2851, 1648, 1479, 1462, 1430, 1396, 1341, 1273, 1229, 1178, 1091, 1043, 928, 789, 751, 716, 653, 630.

HRMS (ESI positive):

Calculated for C$_{20}$H$_{24}$NO [M-I]$^+$ 294.1858; Found 294.1847.

$[α]_D^{20}$+177° (c 0.27, MeOH).

Compound No 33

To a solution of 7.1 g of Compound No 31 (16.4 mmol) in 220 mL of methanol were added of amberlite IRA-400 chloride (56 g) and the mixture was stirred at room temperature for 2 h. After filtration, the solution was concentrated under vacuum to give 5.1 g of Compound No 33 as a white solid without any purification.

Yield: 92%.

Melting point: 180-181° C.

$^1$H NMR δ (300 MHz, CDCl$_3$) (ppm): 7.57 (d, J=6.8 Hz, 1H), 7.33 (dt, J=13.5, 7.9 Hz, 5H), 7.16-7.04 (m, 2H), 6.21 (d, J=5.4 Hz, 1H), 4.43 (dd, J=14.4, 4.4 Hz, 1H), 4.05 (m, 2H), 3.30-3.05 (m, 3H), 2.37 (s, 3H), 1.62 (t, J=7.2 Hz, 3H), 1.18-0.98 (m, 1H), 0.85-0.59 (m, 2H), 0.47-0.32 (m, 1H), 0.24 (m, 1H).

IR (neat) (cm$^{-1}$): λ$_{max}$=3387, 3001, 1627, 1459, 1430, 1395, 1247, 1158, 1108, 1024, 758, 713, 634.

HRMS (ESI positive): Calculated for C$_{22}$H$_{26}$N [M-Cl]$^+$ 304.2065; Found 304.2061.

Compound No 34

Compound No 34 was prepared according to the procedure described for the synthesis of Compound No 33. To a solution of 5.3 g of Compound No 14 (13.1 mmol) in 177 mL of methanol were added amberlite IRA-400 chloride (42.5 g) to give 5.1 g of Compound No 34 as a white solid without purification.

Yield: 93%.

Melting point=218-219° C.

$^1$H NMR δ (300 MHz, CDCl$_3$) (ppm): 7.62 (d, J=7.0 Hz, 1H), 7.42-7.26 (m, 5H), 7.13 (d, J=7.0 Hz, 1H), 7.08 (d, J=7.2 Hz, 1H), 6.24 (d, J=5.2 Hz, 1H), 4.08 (m, 2H), 3.80 (m, 1H), 3.65 (m, 1H), 3.39 (m, 1H), 3.17 (d, J=19.5 Hz, 1H), 2.29 (s, 3H), 1.62-1.46 (m, 6H).

IR (neat) (cm$^{-1}$): λ$_{max}$=3347, 3016, 2972, 1455, 1405, 1237, 1044, 1015, 762, 743.

HRMS (ESI positive): Calculated for C$_{20}$H$_{24}$N [M-Cl]$^+$ 278.1909; Found 278.1904.

Compound No 35

To a solution of 100 mg of (5S,10R)-12-(cyclopropylmethyl)-5-methyl-10,11-dihydro-5H-5,10-epiminodibenzo[a,d][7]annulene (0.36 mmol) in 2 mL of acetonitrile in a microwave-type tube, were added 2.81 mL of propyl iodide (28.8 mmol). The vial is sealed, and the mixture was heated at 75° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 137 mg of Compound No 35 as a yellow solid after purification by silica-gel column chromatography (eluent 90% DCM/ 10% MeOH).

Yield: 85%.

Melting point=203-204° C.

$^1$H NMR δ (300 MHz, CDCl$_3$) (ppm): 7.62 (d, J=6.1 Hz, 1H), 7.47-7.22 (m, 5H), 7.12 (d, J=6.3 Hz, 2H), 6.08 (d, J=4.9 Hz, 1H), 4.07 (m, 1H), 3.79 (t, J=12.6 Hz, 1H), 3.28-3.01 (m, 3H), 2.39 (s, 3H), 2.23 (m, 1H), 1.89 (m, 1H), 1.24 (dd, J=9.6, 4.7 Hz, 2H), 0.93 (t, J=6.2 Hz, 3H), 0.79 (m, 2H), 0.40 (m, 2H).

IR (neat) (cm$^{-1}$): λ$_{max}$=3481, 3001, 1454, 1420, 1384, 1024, 926, 753.

HRMS (ESI positive): Calculated for C$_{23}$H$_{28}$N [M-I]$^+$ 318.2222; Found 318.2213.

Compound No 36

To a solution of 100 mg of (5S,10R)-12-(cyclopropylmethyl)-5-methyl-10,11-dihydro-5H-5,10-epiminodibenzo[a, d][7]annulene (0.36 mmol) in 2 mL of acetonitrile in a microwave-type tube, were added 2.81 mL of butyl iodide (28.8 mmol). The vial is sealed, and the mixture was heated at 75° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 131 mg of Compound No 36 as a yellow solid after purification by silica-gel column chromatography (eluent 90% DCM/ 10% MeOH).

Yield: 79%.

Melting point=171-172° C.

$^1$H NMR δ (300 MHz, CDCl$_3$) (ppm): 7.61 (d, J=7.2 Hz, 1H), 7.34 (dd, J=13.6, 5.3 Hz, 5H), 7.16-7.05 (m, 2H), 6.10 (d, J=4.7 Hz, 1H), 4.28 (dd, J=14.3, 4.8 Hz, 1H), 4.09 (m, 1H), 3.81 (t, J=10.9 Hz, 1H), 3.14 (m, 3H), 2.37 (s, 3H), 2.21 (m, 1H) 1.91 (s, 1H), 1.44-1.14 (m, 3H), 0.93 (t, J=7.3 Hz, 3H), 0.78 (d, J=22.6 Hz, 2H), 0.51-0.41 (m, 1H), 0.39-0.29 (m, 1H).

IR (neat) (cm$^{-1}$): λ$_{max}$=3441, 2962, 2932, 1726, 1449, 1424, 1237, 1024, 758, 738.

HRMS (ESI positive): Calculated for C$_{24}$H$_{30}$N [M-I]$^+$ 332.2378; Found 332.2386.

Compound No 37

To a solution of 56 mg of 2-((5S,10R)-5-methyl-10,11-dihydro-5H-5,10-epiminodibenzo[a,d][7]annulen-12-yl) ethan-1-ol (0.21 mmol) in 1.2 mL of acetonitrile in a microwave-type tube, were added 1.6 mL of propyl iodide (16.8 mmol). The vial is sealed, and the mixture was heated at 90° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 55 mg of Compound No 37 as a yellow solid without purification.

Yield: 60%.

Melting point=221-222° C.

$^1$H NMR δ (300 MHz, CDCl$_3$) (ppm): 7.50 (d, J=7.9 Hz, 1H), 7.35 (dd, J=19.9, 12.5 Hz, 5H), 7.12 (dd, J=13.1, 6.6 Hz, 2H), 5.82 (d, J=4.8 Hz, 1H), 4.55 (t, J=5.4 Hz, 1H), 4.21 (m, 3H), 3.73 (t, J=12.4 Hz, 2H), 3.58 (d, J=15.1 Hz, 1H), 3.34 (s, 1H), 3.05 (d, J=19.1 Hz, 1H), 2.28 (s, 3H), 2.12 (m, 1H), 1.70-1.60 (m, 1H), 0.92 (t, J=7.2 Hz, 3H).

$^{13}$C NMR δ (75 MHz, CDCl$_3$) (ppm): 142.9, 135.3, 134.9, 130.6, 130.3, 130.1, 130.0, 129.5, 128.1, 123.4, 123.1, 120.3, 84.8, 69.7, 60.2, 56.5, 54.9, 32.3, 19.5, 14.3, 11.3.

IR (neat) (cm$^{-1}$): λ$_{max}$=3328, 2957, 2349, 1445, 1034, 748.

Compound No 38

To a solution of 63 mg of 2-((5S,10R)-5-methyl-10,11-dihydro-5H-5,10-epiminodibenzo[a,d][7]annulen-12-yl) ethan-1-ol (0.23 mmol) in 1.3 mL of acetonitrile in a microwave-type tube, were added 2.0 mL of butyl iodide (18.4 mmol). The vial is sealed, and the mixture was heated at 90° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 47 mg of Compound No 38 as a yellow solid without purification.

Yield: 45%.

Melting point=196-197° C.

$^1$H NMR δ (300 MHz, Acetone) (ppm): 7.72 (d, J=6.7 Hz, 1H), 7.61 (d, J=9.0 Hz, 1H), 7.48-7.31 (m, 5H), 7.21 (s, 1H), 5.86 (d, J=5.2 Hz, 1H), 5.01 (t, J=5.4 Hz, 1H), 4.28-4.01 (m, 3H), 3.83 (t, J=11.1 Hz, 1H), 3.68 (m, 2H), 3.53-3.37 (m, 1H), 3.19 (d, J=19.0 Hz, 1H), 2.46 (s, 3H), 2.14 (m, 1H), 1.67 (m, 1H), 1.47-1.21 (m, 2H), 0.89 (t, J=7.3 Hz, 3H).

$^{13}$C NMR δ (75 MHz, Acetone) (ppm): 145.0, 144.5, 137.1, 136.0, 131.0, 130.8, 130.5 (2C), 128.5, 124.9, 124.2, 121.5, 80.7, 7.7, 58.7, 57.0, 55.8, 32.4, 27.9, 20.5, 13.8, 13.5.

IR (neat) (cm$^{-1}$): λ$_{max}$=3304, 2962, 1440, 1034, 736.

Compound No 39

Compound No 39 is prepared according to the general procedure D.

To a solution of 44 mg of 4-((5S,10R)-5-methyl-10,11-dihydro-5H-5,10-epiminodibenzo[a,d][7]annulen-12-yl)butan-1-ol (0.14 mmol) in 0.83 mL of dioxane were added 0.88 mL of ethyl iodide (11.2 mmol) to give 34 mg of Compound No 39 as a white solid without purification.

Yield: 53%.

Melting point=201-202° C.

$^1$H NMR δ (300 MHz, CDCl$_3$) (ppm): 7.59 (d, J=7.4 Hz, 1H), 7.43-7.29 (m, 5H), 7.16 (d, J=6.6 Hz, 1H), 7.09 (d, J=6.9 Hz, 1H), 5.91 (d, J=4.9 Hz, 1H), 3.97 (d, J=13.9 Hz, 2H), 3.68 (m, 4H), 3.37 (dd, J=14.3, 6.7 Hz, 1H), 3.15 (d, J=18.2 Hz, 1H), 3.01 (m, 1H), 2.31 (s, 3H), 2.25 (m, 1H), 2.12-1.99 (m, 1H), 1.54 (dd, J=15.6, 8.2 Hz, 5H).

$^{13}$C NMR δ (75 MHz, CDCl$_3$) (ppm): 144.05, 141.55, 135.51, 134.26, 130.46, 130.35, 130.13, 130.04, 129.74, 128.29, 123.54, 120.33, 83.95, 68.58, 60.33, 53.06, 52.86, 31.82, 29.66, 22.12, 15.08, 11.76.

IR (neat) (cm$^{-1}$): λ$_{max}$=3377, 2912, 1454, 1384, 1069, 1024, 1014, 1000, 767, 748.

HRMS (ESI positive): Calculated for C$_{22}$H$_{28}$NO [M-I]$^+$ 322.2171; Found 322.2167.

Compound No 40

Compound No 40 is prepared according to the general procedure D.

To a solution of 150 mg of (5S,10R)-12-(cyclopropylmethyl)-5-methyl-10,11-dihydro-5H-5,10-epiminodibenzo[a,d][7]annulene (0.54 mmol) in 3.2 mL of dioxane were added 0.21 mL of ethyl iodide (2.72 mmol) to give 38 mg of Compound No 40 as a yellow solid without purification.

Yield: 16%.

Melting point=179-180° C.

$^1$H NMR δ (300 MHz, CDCl$_3$) (ppm): 7.59 (d, J=6.9 Hz, 1H), 7.34 (td, J=14.7, 7.3 Hz, 5H), 7.10 (dd, J=15.7, 7.7 Hz, 2H), 6.48 (d, J=5.8 Hz, 1H), 4.40 (d, J=5.5 Hz, 1H), 4.28 (d, J=14.4 Hz, 2H), 3.88 (dd, J=18.8, 5.3 Hz, 1H), 3.37-3.21 (m, 1H), 3.05 (dd, J=26.7, 17.3 Hz, 2H), 2.37 (s, 3H), 1.26 (t, J=7.1 Hz, 3H), 0.82 (td, J=8.4, 4.0 Hz, 1H), 0.77-0.68 (m, 1H), 0.48-0.38 (m, 1H), 0.00 (dd, J=9.5, 4.3 Hz, 1H).

$^{13}$C NMR (75 MHz, CDCl$_3$) (ppm): 143.3, 139.7, 135.1, 130.5, 130.4, 130.3, 129.8, 128.2, 126.4, 123.8, 123.3, 120.2, 70.1, 59.1, 55.8, 55.4, 49.2, 43.6, 31.6, 15.4, 7.8, 6.8, 5.9.

IR (neat) (cm$^{-1}$): λ$_{max}$=3328, 2998, 2995, 1459, 1424, 1019, 758.

HRMS (ESI positive): Calculated for C$_{22}$H$_{26}$NO [M-I]$^+$ 320.2014; Found 320.1992.

Compound No 41

To a solution of 110 mg of (5S,10R)-12-(cyclopropylmethyl)-5-methyl-10,11-dihydro-5H-5,10-epiminodibenzo[a,d][7]annulene (0.39 mmol) in 2.2 mL of dioxane were added 2.7 mL of propargyl bromide (31.2 mmol). The vial is sealed, and the mixture was heated at 45° C. under stirring for 15 hours. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 123 mg of Compound No 41 as a white solid without purification.

Yield: 79%.

Melting point=168-169° C.

$^1$H NMR δ (300 MHz, CDCl$_3$) (ppm): 7.70 (d, J=6.8 Hz, 1H), 7.37 (dd, J=16.6, 9.8 Hz, 5H), 7.12 (dd, J=11.6, 7.3 Hz, 2H), 6.62 (s, 1H), 4.81 (s, 2H), 3.87 (dd, J=19.0, 5.2 Hz, 1H), 3.70 (dd, J=13.9, 4.6 Hz, 1H), 3.50 (dd, J=13.8, 8.8 Hz, 1H), 3.24 (d, J=18.9 Hz, 1H), 2.92 (s, 1H), 2.40 (s, 3H), 1.49 (m, 1H), 1.02-0.81 (m, 3H), 0.45 (d, J=5.6 Hz, 1H).

IR (neat) (cm$^{-1}$): λ$_{max}$=3310, 2986, 2361, 2181, 2045, 1460, 1047, 767, 717.

HRMS (ESI positive): Calculated for C$_{23}$H$_{24}$N [M-Br]$^+$ 314.1909; Found 314.1909.

Compound No 42

To a solution of 146 mg of 2-((5S,10R)-5-methyl-10,11-dihydro-5H-5,10-epiminodibenzo[a,d][7]annulen-12-yl)ethan-1-ol (0.55 mmol) in 2.9 mL of dioxane were added 3.9 mL of propargyl bromide (44.0 mmol). The vial is sealed, and the mixture was heated at 90° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 177 mg of Compound No 42 as a white solid without purification.

Yield: 84%.

Melting point=201-202° C.

$^1$H NMR δ (300 MHz, CDCl$_3$) (ppm): 7.61-7.50 (m, 1H), 7.35 (dt, J=17.2, 8.3 Hz, 5H), 7.14 (d, J=6.4 Hz, 2H), 6.43 (d, J=5.1 Hz, 1H), 5.69-5.59 (m, 1H), 5.52 (dd, J=17.4, 2.4 Hz, 1H), 4.75-4.59 (m, 1H), 4.37 (dd, J=19.1, 5.4 Hz, 1H), 4.24 (d, J=17.9 Hz, 1H), 3.98 (d, J=14.4 Hz, 1H), 3.64 (t, J=13.7 Hz, 2H), 3.06 (d, J=18.8 Hz, 1H), 2.96 (d, J=2.3 Hz, 1H), 2.35 (s, 3H).

IR (neat) (cm$^{-1}$): λ$_{max}$=3169, 2962, 2117, 1445, 1400, 1346, 1089, 1094, 945, 846, 782, 767, 688.

Compound No 43

To a solution of 100 mg of (5S,10R)-12-(cyclopropylmethyl)-5-methyl-10,11-dihydro-5H-5,10-epiminodibenzo[a,d][7]annulene (0.36 mmol) in 2 mL of acetonitrile were added 1.2 mL of allyl bromide (14.4 mmol). The vial is sealed, and the mixture was heated at 50° C. under stirring for 15 hours. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 97 mg of Compound No 43 as a white solid without purification.

Yield: 68%.

Melting point=131-132° C.

$^1$H NMR δ (300 MHz, CDCl$_3$) (ppm): 7.48 (dd, J=5.8, 2.5 Hz, 1H), 7.43-7.38 (m, 1H), 7.36-7.25 (m, 4H), 7.17-7.08 (m, 2H), 6.47-6.26 (m, 1H), 5.91 (d, J=5.0 Hz, 1H), 5.54 (d, J=10.1 Hz, 1H), 5.21 (d, J=16.7 Hz, 1H), 4.75 (dd, J=13.4, 5.3 Hz, 1H), 4.19-4.10 (m, 1H), 3.97 (dd, J=19.0, 5.4 Hz, 1H), 3.71 (dd, J=13.5, 8.8 Hz, 1H), 3.29 (dd, J=14.1, 8.8 Hz, 1H), 3.13 (d, J=19.2 Hz, 1H), 2.41 (s, 3H), 1.32-1.18 (m, 1H), 0.85-0.69 (m, 2H), 0.45 (d, J=3.2 Hz, 2H).

$^{13}$C NMR δ (75 MHz, CDCl$_3$) (ppm): 143.6, 135.4, 134.3, 130.3, 130.1, 130.0, 129.9, 128.1, 127.1, 126.2, 123.4, 123.3, 120.4, 82.9, 69.0, 59.2, 57.8, 31.8, 15.1, 7.9, 6.7, 5.4.

IR (neat) (cm$^{-1}$): λ$_{max}$=3495, 3005, 1731, 1621, 1461, 1448, 1393, 1248, 1082, 994, 790, 768.

Compound No 44

To a solution of 50 mg of 2-((5S,10R)-5-methyl-10,11-dihydro-5H-5,10-epiminodibenzo[a,d][7]annulen-12-yl) ethan-1-ol (0.18 mmol) in 1 mL of acetonitrile were added 0.65 mL of allyl bromide (7.2 mmol). The vial is sealed, and the mixture was heated at 90° C. under stirring for 4 days. After being allowed to cool to room temperature, the precipitate formed was increased by addition of pentane and filtered on sintered filter and washed with ethyl acetate, then recovered by dissolution in dichloromethane. The obtained solution was concentrated under reduced pressure (10 mbar) to give 61 mg of Compound No 44 as a white solid without purification.

Yield: 87%.

Melting point=196-197° C.

$^1$H NMR δ (300 MHz, CDCl$_3$) (ppm): 7.34 (m, 6H), 7.17-7.07 (m, 2H), 6.20 (dt, J=15.2, 9.7 Hz, 1H), 5.81 (d, J=5.1 Hz, 1H), 5.45 (dd, J=13.5, 7.7 Hz, 2H), 5.23 (d, J=16.6 Hz, 1H), 4.65 (dd, J=14.0, 4.5 Hz, 1H), 4.35 (dd, J=12.6, 6.6 Hz, 1H), 4.22 (dd, J=19.0, 5.6 Hz, 1H), 4.14-3.99 (m, 2H), 3.67 (s, 2H), 3.04 (d, J=18.7 Hz, 1H), 2.32 (s, 3H).

IR (neat) (cm$^{-1}$): λ$_{max}$=3246, 1461, 1434, 1082, 1434, 1082, 924, 766, 751.

Compound No 45

To a solution at 0° C. of 65 mg of 2-((5S,10R)-5-methyl-10,11-dihydro-5H-5,10-epiminodibenzo[a,d][7]annulen-12-yl)ethan-1-ol (0.24 mmol) in 1 mL of tetrahydrofuran were added 6 mg of sodium hydride (0.26 mmol). The solution was stirred for 30 min and 57 μL of methyl iodide were added. The mixture was stirred at room temperature for 17 hours and then diluted in diethyl ether. The organic was washed with water and a saturated solution of sodium chloride. The organic layer was dried over magnesium sulfate and concentrated under reduced pressure (10 mbar) to give Compound No 45 as a white solid after purification by silica-gel column chromatography (eluent 90% DCM/10% MeOH).

Yield: 28%.

Melting point=162-163° C.

$^1$H NMR δ (300 MHz, CDCl$_3$) (ppm): 7.54-7.48 (m, 1H), 7.41-7.28 (m, 5H), 7.11 (dd, J=12.9, 7.0 Hz, 2H), 5.61 (d, J=5.3 Hz, 1H), 4.27-4.08 (m, 2H), 3.98-3.85 (m, 2H), 3.56 (dd, J=18.6, 8.2 Hz, 2H), 3.48 (s, 1H), 3.38 (s, 3H), 3.05 (d, J=18.9 Hz, 1H), 2.33 (s, 3H).

$^{13}$C NMR δ (75 MHz, CDCl$_3$) (ppm): 142.26, 135.0 (2C), 130.3, 130.2, 130.1, 130.0, 129.0, 128.3, 123.8, 123.5, 120.9, 83.7, 74.1, 67.2, 59.7, 53.0, 45.6, 32.0, 14.1.

IR (neat) (cm$^{-1}$): λ$_{max}$=3491, 2927, 1474, 1449, 1425, 1395, 1257, 1202, 1108, 1024, 950, 767, 743, 713.

HRMS (ESI positive): Calculated for C$_{20}$H$_{24}$NO [M-I]$^+$ 294.1858; Found 294.1852.

Compound No 46

To a solution of 900 mg of (+)-MK801 maleate (2.67 mmol) in 30 mL of acetonitrile were added 1.10 g of potassium carbonate (8.00 mmol) and 0.70 mL of allyl bromide (8.00 mmol). The resulting mixture was refluxed for 6 hours, allowed to cool down at room temperature and filtrated using dichloromethane as solvent. After evaporation, the crude product was purified by silica gel chromatography (dichloromethane/methanol: 97.5/2.5 to 95/5) to give 122 mg of Compound No 46 as a white brown solid.

Yield: 12%.

$^1$H NMR δ (300 MHz, CDCl$_3$) (ppm): 7.53-7.50 (m, 1H), 7.42-7.28 (m, 5H), 7.13-7.11 (m, 2H), 6.35-6.11 (m, 2H), 5.95 (d, J=4.9 Hz, 1H), 5.65-5.55 (m, 3H), 5.27 (d, J=16.7 Hz, 1H), 4.67 (dd, J=14.2, 6.3 Hz, 1H), 4.53 (dd, J=13.5, 5.4 Hz, 1H), 4.36 (dd, J=14.2, 7.9 Hz, 1H), 4.06 (dd, J=19.3, 5.1 Hz, 1H), 3.73 (dd, J=13.4, 8.7 Hz, 1H), 3.17 (d, J=19.2 Hz, 1H), 2.35 (s, 3H).

MS (ESI positive): 302 [C$_{22}$H$_{24}$N]$^+$

Compound No 47

Compound No 47 was prepared according to the procedure described for the synthesis of Compound No 33. To a solution of 122 mg of Compound No 46 (0.32 mmol) in 14 mL of methanol were added amberlite IRA-400 chloride (1.02 g) to give 100 mg of Compound No 47 as a white brown solid without purification.

Yield: 92%.

$^1$H NMR δ (300 MHz, CDCl$_3$) (ppm): 7.49-7.46 (m, 1H), 7.39-7.25 (m, 5H), 7.14-7.07 (m, 2H), 6.40-6.26 (m, 1H), 6.19-6.06 (m, 1H), 5.99 (d, J=5.0 Hz, 1H), 5.63-5.54 (m, 3H), 5.24 (d, J=16.9 Hz, 1H), 4.92 (dd, J=14.1, 6.4, 1H), 4.53 (dd, J=5.4, 13.3 Hz, 1H), 4.39 (dd, J=14.2, 7.9 Hz, 1H), 4.11 (dd, J=5.4, 19.1 Hz, 1H), 3.73 (dd, J=13.5, 8.8 Hz, 1H), 3.14 (d, J=19.3 Hz, 1H), 2.32 (s, 3H).

Compound No 48

To a solution of 400 mg of 2-((5S,10R)-5-methyl-10,11-dihydro-5H-5,10-epiminodibenzo[a,d][7]annulen-12-yl) ethanol (1.50 mmol) in 7.5 mL of dioxane were added 1.30 g of potassium carbonate (15.0 mmol) and 1.20 mL of 2-iodoethanol (15.3 mmol). The resulting mixture was stirred and heated in a sealed tube at 100° C. for 96 hours, allowed to cool down at room temperature and filtrated using dichloromethane as solvent. After evaporation, the crude product was purified by silica gel chromatography (dichloromethane/methanol: 97.5/2.5 to 95/5) to give 300 mg of Compound No 48 as a white solid.

Yield: 46%.

$^1$H NMR δ (300 MHz, CDCl$_3$) (ppm): 7.57-7.55 (m, 1H), 7.40-7.26 (m, 5H), 7.13-7.08 (m, 2H), 5.99 (d, J=4.9 Hz, 1H), 4.34-3.89 (m, 9H), 3.63-3.59 (m, 1H), 3.43-3.37 (m, 1H), 3.08 (d, J=18.9 Hz, 1H), 2.32 (s, 3H).

The table 1 below illustrates Compounds No 1 to No 53 of the invention:

TABLE 1

[Structure: dibenzo-azabicyclic cation with R1-(CH2)n- and R2 substituents on N+, CH3 at bridgehead, counterion X-]

| No | Formula | n | R₁ | R₂ | Chirality | Counterion X⁻ |
|---|---|---|---|---|---|---|
| 1 | [structure] | 1 | —H | —CH₃ | (+) | I⁻ |
| 2 | [structure] | 1 | —CH₃ | —CH₃ | (+) | I⁻ |
| 3 | [structure] | 3 | —CH₃ | —CH₃ | (+) | I⁻ |
| 4 | [structure] | 1 | —CH(—CH₃)₂ | —CH₃ | (+) | I⁻ |
| 5 | [structure] | 1 | -cyclopropyl | —CH₃ | (+) | I⁻ |

TABLE 1-continued

| No | Formula | n | R₁ | R₂ | Chirality | Counterion X⁻ |
|---|---|---|---|---|---|---|
| 6 | | 1 | -cyclopentyl | —CH₃ | (+) | I⁻ |
| 7 | | 1 | —C(=NH)—OH | —CH₃ | (+) | I⁻ |
| 8 | | 1 | -4-fluorophenyl | —CH₃ | (+) | I⁻ |
| 9 | | 1 | -3-CF₃-phenyl | —CH₃ | (+) | I⁻ |

TABLE 1-continued

| No | Formula | n | R₁ | R₂ | Chirality | Counterion X⁻ |
|---|---|---|---|---|---|---|
| 10 | | 2 | —CH(—CH₃)₂ | —CH₃ | (+) | I⁻ |
| 11 | | 2 | —CH₃ | —CH₃ | (+) | I⁻ |
| 12 | | 5 | —CH₃ | —CH₃ | (+) | I⁻ |
| 13 | | 1 | —CH(—CH₃)—CH₂—CH₃ | —CH₃ | (+) | I⁻ |

TABLE 1-continued

[Structure: dibenzazepine-type bicyclic quaternary ammonium with R1-(CH2)n and R2 substituents on N+, X- counterion, and CH3 at bridgehead]

| No | Formula | n | R₁ | R₂ | Chirality | Counterion X⁻ |
|---|---|---|---|---|---|---|
| 14 | [structure] | 1 | —CH₃ | —CH₂—CH₃ | (+) | I⁻ |
| 15 | [structure] | 1 | -cyclohexyl | —CH₃ | (+) | I⁻ |
| 16 | [structure] | 1 | -phenyl | —CH₃ | (+) | I⁻ |
| 17 | [structure] | 1 | -cyclobutyl | —CH₃ | (+) | I⁻ |

TABLE 1-continued
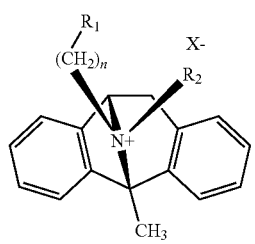
| No | Formula | n | R$_1$ | R$_2$ | Chirality | Counterion X$^-$ |
|---|---|---|---|---|---|---|
| 18 | | 1 | -cyclopropyl-phenyl | —CH$_3$ | (+) | I$^-$ |
| 19 | | 1 | -4-CH$_3$-phenyl | —CH$_3$ | (+) | I$^-$ |
| 20 | | 1 | -4-C(—CH$_3$)$_3$-phenyl | —CH$_3$ | (+) | I$^-$ |

TABLE 1-continued

| No | Formula | n | R₁ | R₂ | Chirality | Counterion X⁻ |
|----|---------|---|-----|-----|-----------|----------------|
| 21 | (structure) | 1 | -4-OCH₃-phenyl | —CH₃ | (+) | I⁻ |
| 22 | (structure) | 1 | -4-chlorophenyl | —CH₃ | (+) | I⁻ |
| 23 | (structure) | 1 | -2-chlorophenyl | —CH₃ | (+) | I⁻ |
| 24 | (structure) | 1 | -2-CH₃-phenyl | —CH₃ | (+) | I⁻ |

TABLE 1-continued

| No | Formula | n | R₁ | R₂ | Chirality | Counterion X⁻ |
|---|---|---|---|---|---|---|
| 25 | | 2 | —OH | —CH₃ | (+) | I⁻ |
| 26 | | 2 | —OH | —CH₂—CH₃ | (+) | I⁻ |
| 27 | | 2 | —OH | —CH₂—CH₃ | (±) | I⁻ |
| 28 | | 1 | —CN | —CH₃ | (+) | I⁻ |

TABLE 1-continued

| No | Formula | n | R₁ | R₂ | Chirality | Counterion X⁻ |
|---|---|---|---|---|---|---|
| 29 | | 2 | —NH—CO—CH₃ | —CH₃ | (+) | I⁻ |
| 30 | | 1 | -cyclopropyl-4-chlorophenyl | —CH₃ | (+) | I⁻ |
| 31 | | 1 | -cyclopropyl | —CH₂—CH₃ | (+) | I⁻ |
| 32 | | 2 | —OH | —CH₂—CH₃ | (+) | Cl⁻ |

TABLE 1-continued
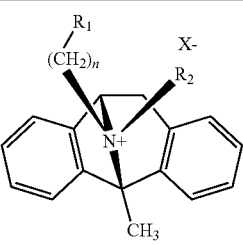
| No | Formula | n | R₁ | R₂ | Chirality | Counterion X⁻ |
|----|---------|---|----|----|-----------|---------------|
| 33 | 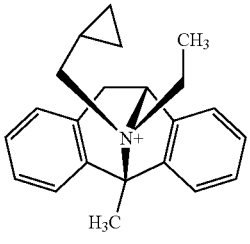 [SMILES: CC[N@@+]1(CC2CC2)[C@@H]2Cc3ccccc3[C@@]1(C)c1ccccc12] | 1 | -cyclopropyl | —CH₂—CH₃ | (+) | Cl⁻ |
| 34 | 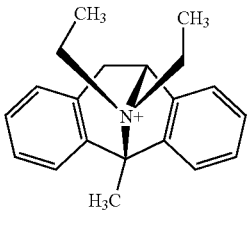 | 1 | —CH₃ | —CH₂—CH₃ | (+) | Cl⁻ |
| 35 | 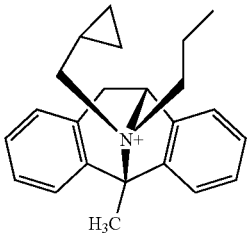 [SMILES: CCC[N@@+]1(CC2CC2)[C@@H]2Cc3ccccc3[C@@]1(C)c1ccccc12] | 1 | -cyclopropyl | —(CH₂)₂—CH₃ | (+) | I⁻ |
| 36 | 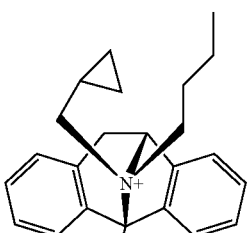 | 1 | -cyclopropyl | —(CH₂)₃—CH₃ | (+) | I⁻ |
| 37 | 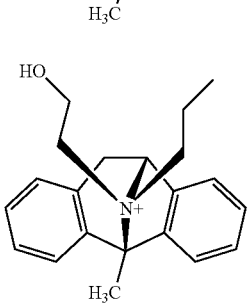 [SMILES: CCOCC[N@+]1(CC)[C@@H]2Cc3ccccc3[C@@]1(C)c1ccccc12] | 2 | —OH | —(CH₂)₂—CH₃ | (+) | I⁻ |

TABLE 1-continued

[Structure: dibenzazepine/tricyclic core with N+ bearing (CH₂)ₙR₁ and R₂ substituents, with CH₃ at bottom bridging carbon; counterion X⁻]

| No | Formula | n | R₁ | R₂ | Chirality | Counterion X⁻ |
|---|---|---|---|---|---|---|
| 38 | [structure] | 2 | —OH | —(CH₂)₃—CH₃ | (+) | I⁻ |
| 39 | [structure] | 4 | —OH | —CH₂—CH₃ | (+) | I⁻ |
| 40 | [structure] | 1 | -cyclopropyl | —(CH₂)₂—OH | (+) | I⁻ |
| 41 | [structure] | 1 | -cyclopropyl | —CH₂—C≡CH | (+) | Br⁻ |

TABLE 1-continued

| No | Formula | n | R₁ | R₂ | Chirality | Counterion X⁻ |
|---|---|---|---|---|---|---|
| 42 | | 2 | —OH | —CH₂—C≡CH | (+) | Br⁻ |
| 43 | | 1 | -cyclopropyl | —CH₂—CH=CH₂ | (+) | Br⁻ |
| 44 | | 2 | —OH | —CH₂—CH=CH₂ | (+) | Br⁻ |
| 45 | | 2 | —O—CH₃ | —CH₃ | (+) | I⁻ |
| 46 | | 1 | —CH=CH₂ | —CH₂—CH=CH₂ | (+) | Br⁻ |

TABLE 1-continued

| No | Formula | n | R₁ | R₂ | Chirality | Counterion X⁻ |
|---|---|---|---|---|---|---|
| 47 | | 1 | —CH=CH₂ | —CH₂—CH=CH₂ | (+) | Cl⁻ |
| 48 | | 2 | —OH | —(CH₂)₂—OH | (+) | I⁻ |
| 49 | | 1 | —CH₃ | —CH(—CH₃)—CH₂—OH | (+) | Cl⁻ |
| 50 | | 2 | —O—CH₃ | —CH₂—CH₃ | (+) | Cl⁻ |

TABLE 1-continued

| No | Formula | n | $R_1$ | $R_2$ | Chirality | Counterion $X^-$ |
|---|---|---|---|---|---|---|
| 51 | | 2 | —O—CH$_2$—CH$_3$ | —CH$_2$—CH$_3$ | (+) | Cl$^-$ |
| 52 | | 2 | —F | —CH$_2$—CH$_3$ | (+) | Cl$^-$ |
| 53 | | 2 | —N(CH$_3$)$_2$ | —CH$_2$—CH$_3$ | (+) | Cl$^-$ |

The table 2 below illustrates Compounds No 54 to No 56 of the invention:

TABLE 2

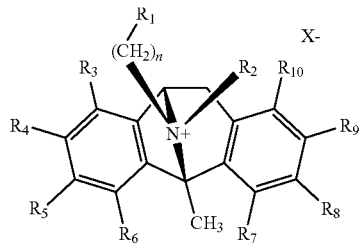

| No | Formula | n | $R_1$ | $R_2$ | $R_3$ | $R_4$ | $R_5$, $R_6$, $R_7$ et $R_8$ | $R_9$ | $R_{10}$ | Chirality | Counter ion $X^-$ |
|---|---|---|---|---|---|---|---|---|---|---|---|
| 54 | | 1 | —H | —CH$_3$ | —H | —H | —H | —CH$_3$ | —H | (+) | I$^-$ |
| 55 | | 2 | —CH$_3$ | —CH$_2$—CH$_3$ | —H | —H | —H | —CH$_3$ | —H | (+) | I$^-$ |
| 56 | | 1 | —H | —CH$_3$ | —H | —O—CH$_3$ | —H | —H | —H | (+) | I$^-$ |

The compounds according to the invention were the subject of pharmacological assays.

Example 2

Role of NMDA Receptors in the Development of Pulmonary Hypertension

To understand the functional importance of NMDARs in smooth muscle cells, the Grin1 gene (encoding the obligatory GluN1 subunit) has been deleted from the smooth muscle cells of mice. These knock out mice for NMDAR in PASMC were produced breeding mice expressing Cre recombinase in smooth muscle cells with foxed GRIN1 mice (GRIN1: gene coding for GluN1 ubiquitous subunit of NMDARs).

Under chronic hypoxia (FiO$_2$ 10%, 3 weeks), KO mice develop an attenuated form of PH compared to control mice, with a decreased right ventricular pressure and cardiac hypertrophy (Fulton index) (FIG. 1). In FIG. 1, P<0.01 and p<0.001 in KO mice compared to wild type under hypoxia, for right ventricular systolic pressure and Fulton index, respectively.

After chronic hypoxia (FiO$_2$ 10%, 3 weeks), KO mice also have a decreased muscularization of small vessels (diameter<50 μm) compared to control mice (FIG. 2). Moreover, KO mice present less muscularized large vessels (75 μm<diameter<125 μm) in both normoxic and hypoxic conditions compared to control mice (FIG. 2).

These results indicate that knocking out NMDAR in PASMC attenuates pulmonary vascular cell remodeling, cardiac remodeling and PH in hypoxic mice. Thus, PASMC NMDA receptors contribute to pulmonary vascular cell remodeling, cardiac remodeling and to pulmonary hypertension.

Example 3

In Vivo Brain Penetration Measurements

Compounds of the present invention provide a mean to prevent Blood-Brain Barrier. This assumption has been verified on rats.

Among methods addressing central nervous system penetration in drug discovery, in vivo equilibrium distribution between blood and brain in rodents is the most commonly used parameter to evaluate brain penetration.

This parameter is defined as the ratio of concentrations in brain and blood, $Kp_{"brain"}$ ($C_{brain}/C_{plasma}$) or log(BB). Log (BB) is the logarithm of the ratio of the steady-state total concentration of a compound in the brain to that in the blood/plasma, $\log(BB)=\log(C_{brain}/C_{plasma})$. This parameter depends upon the passive diffusion characteristics, the implication of membrane transporters at the BBB level and the relative drug binding affinity differences between the plasma proteins and brain tissue. Generally, compounds with a brain/plasma ratio of greater than 0.5 are considered to have sufficient access to the CNS. Thus, compounds with a value greater than 1 freely cross the BBB.

Thus, the brain penetration of MK801, Compound No 1 and Compound No 26 was measured in rat by establishing the brain/plasma ratio, Kp.."$_{brain}$" in triplicate (3 rats/Compound). The enclosed FIG. 3 shows the results on calculation of the Kp.."$_{brain}$" for the three compounds MK801, Compound No 1 and Compound No 26.

The Kp.."$_{brain}$" value (defined as the total brain/plasma concentration ratio at steady state) was calculated in 3 rats for each compound MK801, Compound No 1 and Compound No 26. Compounds No 1 and No 26 present a very low Kp.."$_{brain}$" value as compared to MK801 (0.3±0.03 and 0.4±0.08 versus 17.7±1.75).

In conclusion, as known and previously described, MK801 penetrates freely across the BBB and intensively penetrate the CNS in rat. As we expected, due to the presence of a quaternary ammonium and as demonstrated by the Kp.."$_{brain}$" values, the Compounds No 1 and No 26 do not penetrate the CNS in rat.

Example 4

In Vitro Activity: Evaluation of NMDAR Blocking Activity Using Patch-Clamp

Previous studies have shown that the NMDAR exists in the peripheral vasculature.

All NMDAR subunits were examined by RT-PCR and sequencing in the peripheral endothelium and peripheral vascular smooth muscle cells. The sequences of these NMDAR subunits in both vascular cells showed a high similarity if not identity to the sequences of brain NMDAR (Chen H et al, *J Vasc Surg* 2005, Qureshi I et al *Vasc Med* 2005).

The molecules described herein were tested in serial concentrations ranging from 1 nM to 100 μM for their NMDAR blocking activity using patch-clamp.

Whole-cell voltage clamp recordings from rat hippocampal neurons were then used to calculate $IC_{50}$ for each molecule. The $IC_{50}$ is the concentration of an inhibitor where the response (or binding) is reduced by half.

NMDAR Antagonist Activity of Selected Compounds

| Compound | $IC_{50}$ (μM) |
| --- | --- |
| Dizocilpine ((+)-MK801 maleate) | 0.29 |
| Compound No1 | 0.65 |
| Compound No2 | 0.57 |
| Compound No3 | 0.50 |
| Compound No4 | 0.82 |
| Compound No5 | 0.40 |
| Compound No6 | 1.10 |
| Compound No26 | 0.4 |
| Compound No27 | 0.36 |
| Compound No31 | 0.27 |

The results show that the parent molecule dizocilpine had an $IC_{50}$ of 0.29 μM, which is consistent with its known antagonist activity. Compounds of the present invention have an activity ranging from 0.27 to 1.10 μM. Of interest, results obtained with Compound No 31 ($IC_{50}$=0.27 μM), Compound No 27 ($IC_{50}$=0.36 μM), and Compounds No 5 and No 26 ($IC_{50}$=0.4 μM) clearly demonstrate that structural modification on the nitrogen atom of dizocilpine is not deleterious for activity.

The invention claimed is:

1. Compound of formula (I):

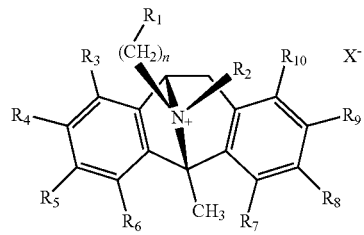

wherein:

$R_1$ represents a cyclopropyl group;

$R_2$ represents a ($C_1$-$C_{10}$)alkyl group;

n is 1;

$R_3$, $R_4$, $R_5$, $R_6$, $R_7$, $R_8$, $R_9$ and $R_{10}$ represent a hydrogen atom; and $X^-$ is an anionic counterion selected from the group consisting of $I^-$, $Cl^-$, $Br^-$ and $OH^-$.

2. Compound according to claim 1, wherein $R_2$ represents a methyl group or an ethyl group.

3. Compound according to claim 1, wherein the anionic counterion $X^-$ is selected from the group consisting of $I^-$ and $Cl^-$.

4. A pharmaceutical composition comprising at least one compound according to claim 1, and at least one pharmaceutically acceptable excipient.

5. A method for A method for treating a disease or condition in a subject comprising administering to the subject a compound according to claim 1, wherein the disease or the condition is pulmonary hypertension.

6. A method for treating a disease or condition in a subject comprising administering to the subject a compound according to the claim 1, wherein the disease or the condition is selected from the group consisting of pulmonary arterial hypertension and thromboembolic pulmonary hypertension.

7. A method for treating a disease in a subject comprising administering to the subject a compound according to claim 1, wherein the disease is pulmonary arterial hypertension.

8. Compound according to claim 1, chosen from:

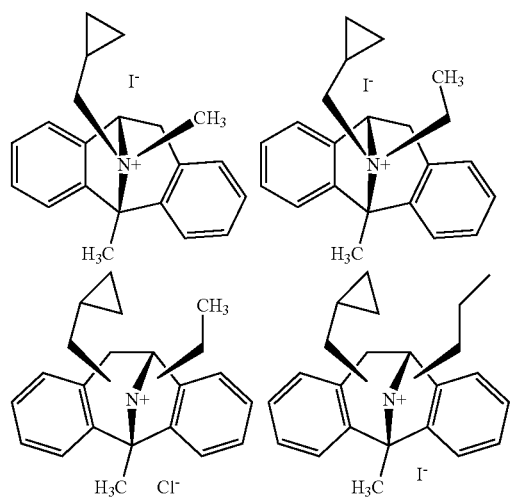

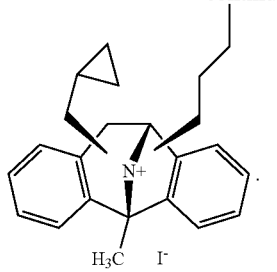
9. Compound according to claim 1, wherein $R_2$ represents a methyl group.
10. Compound according to claim 1, wherein $R_2$ represents an ethyl group.
11. Compound according to claim 1, wherein $X^-$ is $I^-$.
12. Compound according to claim 1, wherein $X^-$ is $Cl^-$.
13. Compound according to claim 1, wherein $X^-$ is $Br^-$.
14. Compound according to claim 1, wherein $X^-$ is $OH^-$.
* * * * *